US006838241B1

(12) United States Patent
Tang et al.

(10) Patent No.: US 6,838,241 B1
(45) Date of Patent: Jan. 4, 2005

(54) PROTEIN TRANSPORT-ASSOCIATED MOLECULES

(75) Inventors: Y. Tom Tang, San Jose, CA (US); Preeti Lal, Santa Clara, CA (US); Olga Bandman, Mountain View, CA (US); Henry Yue, Sunnyvale, CA (US); Neil C. Corley, Castro Valley, CA (US); Karl J. Guegler, Menlo Park, CA (US); Gina A. Gorgone, Boulder Creek, CA (US); Mariah R. Baughn, San Leandro, CA (US); Chandra Patterson, Menlo Park, CA (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 09/763,902

(22) PCT Filed: Aug. 26, 1999

(86) PCT No.: PCT/US99/19616

§ 371 (c)(1),
(2), (4) Date: Jun. 13, 2001

(87) PCT Pub. No.: WO00/12703

PCT Pub. Date: Mar. 9, 2000

Related U.S. Application Data

(60) Provisional application No. 60/098,206, filed on Aug. 27, 1998.

(51) Int. Cl.[7] .............................. C12Q 1/68; C12P 21/02; C07H 21/04
(52) U.S. Cl. ........................... 435/6; 435/69.1; 435/325; 435/419; 435/252.3; 435/254.11; 435/320.1; 536/23.1; 536/24.31
(58) Field of Search .................... 435/6, 69.1, 320.1, 435/325, 419, 252.3, 254.11; 536/23.1, 24.31, 24.33; 530/350

(56) References Cited

PUBLICATIONS

Kain et al. J. Biol. Chem. vol. 273, No. 2, pp. 981–988 (1998).*
GenBank Accession No. CAA762839; GI 1041643 (Aug. 15, 1996).
GenBank Accession No. X91651; GI 1041642 (Aug. 15, 1996).
Direct Submission, Haft et al., NCBI Database, Accession No. AF065482 (GI 3152937), May 23, 1998.
Haft et al., "Identification of a Family of Sorting Nexin Molecules and Characterization of Their Association with Receptors", Molecular and Cellular Biology 18(12) 7278–7287 (Dec. 1998).
Direct Submission, Kurten et al., NCBI Database, Accession No. AF043453 (GI 2827433), Feb. 1, 1998.
Direct Submission, Kramer et al., NCBI Database, Accession No. AAC09299 (GI 3005087), Mar. 16, 1998.
KraEmer et al., "Genetic Analysis of hook, a Gene Required for Endocytic Traficking in Drosophila", Genetics 151:675–684 (Feb. 1999).
Direct Submission, Schuermann et al., NCBI Database, Accession No. CAA55339 (GI 929830) Aug. 3, 1995.

* cited by examiner

Primary Examiner—Robert A. Wax
(74) Attorney, Agent, or Firm—Foley & Lardner, LLP

(57) ABSTRACT

The invention provides human protein transport molecules (PTAM) and polynucleotides which identify and encode PTAM. The invention also provides expression vectors, host cells, antibodies, agonists, and antagonists. The invention also provides methods for diagnosing, treating, or preventing disorders associated with expression of PTAM.

11 Claims, No Drawings

PROTEIN TRANSPORT-ASSOCIATED MOLECULES

This application is the National Stage of International Application No. PCT/US99/19616, filed on Aug. 26, 1999, which claims the benefit under 35 U.S.C. § 119(e) of U.S. Provisional Application Ser. No. 60/098,206, filed Aug. 27, 1998, the contents all of which are hereby incorporated herein by reference.

TECHNICAL FIELD

This invention relates to nucleic acid and amino acid sequences of protein transport-associated molecules and to the use of these sequences in the diagnosis, treatment, and prevention of cell proliferative and secretory disorders.

BACKGROUND OF THE INVENTION

The organization of a cell is designed for optimal structure and function. Each molecule produced by the cell must be targeted to the appropriate subcellular location. To be properly localized, each molecule must contain information which provides its cellular address. Trafficking machinery can use this information to appropriately transport the molecule to its destination. This is a dynamic process, and the location of a molecule can change over time. Defects in any step involving a molecule's proper localization can result in a disorder, such as diabetes or Alzheimer's disease. (James, D. E., and Piper, R. C. (1994) J. Cell Biol. 126:1123–1126; and Nordstedt, C., et al. (1993) J. Biol. Chem. 268:608–612.)

The information that provides the address for targeting resides within the primary structure of the protein. Certain amino acid sequences act as "delivery codes" during the processing or recycling of a molecule and assure that the molecule is properly localized. Several motifs have been identified. The two principal motifs are the nuclear localization signal and signal peptide. Nuclear localization signals (NLS) consist of short stretches of amino acids enriched in basic residues. NLS are found on proteins that are targeted to the nucleus, such as the glucocorticoid receptor. The NLS is recognized by the NLS receptor, importin, which then interacts with the monomeric GTP-binding protein Ran. This NLS protein/receptor/Ran complex navigates the nuclear pore with the help of the homodimeric protein nuclear transport factor 2 (NTF2). NTF2 binds to the GDP-bound form of Ran and to multiple proteins of the nuclear pore complex, such as p62.

Signal peptides are found on proteins that are targeted to the endoplasmic reticulum (ER). Signal peptides consist of stretches of amino acids enriched in hydrophobic residues. Signal peptides are usually found at the extreme N-terminus of the protein and are recognized by a cytosolic signal-recognition peptide (SRP). The SRP binds to the signal peptide and to an SRP receptor, an integral membrane protein in the ER. Once bound to the SRP receptor, the newly formed protein containing the signal peptide is translocated across the ER membrane. Proteins containing signal peptides may end up inserted into the lipid bilayer, or they may end up in the lumen of an organelle or secreted from the cell.

Proteins may also contain separate motifs that specify delivery or retention in a subcellular location. For example, the trans-Golgi network integral membrane protein TGN38 cycles between the trans-Golgi network (TGN) and the plasma membrane. TGN38 contains two separate motifs. One motif, located within the cytoplasmic tail, is responsible for delivery to the Golgi. A second motif, located within the hydrophobic membrane-spanning region, is responsible for retention of the protein in the TGN. (Stephens, D. J., et al. (1997) J. Biol. Chem. 272:14104–14109.) Modification of the motif may alter the address for a protein and cause it to be relocalized. For example, plasma membrane receptors, such as the epidermal growth factor (EGF) receptor and the T-cell receptor (TCR), contain targeting motifs which, when ligand binds to the receptor, become phosphorylated. Phosphorylation of the targeting motif results in internalization and delivery of the receptor to the lysosome for degradation. (Dietrich, J. et al. (1994) EMBO J. 13:2156–2166.)

The information provided by the amino acid motifs is used by the trafficking machinery to sequester and package the protein into vesicles, and then deliver it to the appropriate location. Sorting nexin-1 (SNX1) is an example of a protein involved in the recognition of motifs involved in lysosomal targeting. Molecules targeted for the lysosome that require SNX1 include the carboxypeptidase Y sorting receptor and the EGF receptor. In the absence of SNX1, these molecules become mislocalized. (Kurten, R. C., Cadena, D. L., and Gill, G. N. (1996) Science 272:1008–1010; and Horazdovsky, B. F. et al. (1997) Mol. Biol. Cell 8:1529–1541.) The adaptor protein (AP) complex, which triggers assembly of clathrin on membranes to form vesicles, is also involved in sequestration of proteins for delivery to subcellular locations. AP-1 vesicles, which form at the Golgi, include cation-independent and cation-dependent mannose-6-phosphate receptors (MPRs). These vesicles are delivered to the lysosome. AP-2 vesicles, which form at the plasma membrane, include TGN38 (Stephens, supra) and ligand-bound TCR (Dietrich, supra.) TGN38-containing vesicles are delivered to the TGN and TCR-containing vesicles are delivered to the lysosome.

Once molecules containing targeting motifs have been sequestered and packaged into vesicles, the vesicles need to be delivered to the appropriate location. This delivery process involves another set of proteins. The Rab family of GTPases are involved in this process via a mechanism not clearly understood. Several Rab proteins have been described, each associated with a particular organelle. For example, Rab3 is associated with the plasma membrane, Rab4 with the sorting endosome, and Rab11 with the recycling endosome. There are also Rabs specific to cell types and functions. For example, Rab3A is specifically involved in synaptic vesicle exocytosis in stimulated nerve cells, and Rab4b is involved in glucose transporter-4 (GluT4) translocation in insulin-stimulated adipocytes. (James and Piper, supra.)

The discovery of new protein transport associated molecules and the polynucleotides encoding them satisfies a need in the art by providing new compositions which are useful in the diagnosis, prevention, and treatment of cell proliferative and secretory disorders.

SUMMARY OF THE INVENTION

The invention features substantially purified polypeptides, protein transport-associated molecules, referred to collectively as "PTAM". In one aspect, the invention provides a substantially purified polypeptide comprising an amino acid sequence selected from the group consisting of SEQ ID NO: 1, SEQ ID NO:2, SEQ ID NO:3, SEQ ID NO:4, SEQ ID NO:5, SEQ ID NO:6, SEQ ID NO:7, SEQ ID NO:8 (SEQ ID NO: 1–8), and fragments thereof.

The invention further provides a substantially purified variant having at least 90% amino acid identity to at least one of the amino acid sequences selected from the group consisting of SEQ ID NO:1–8, and fragments thereof. The invention also provides an isolated and purified polynucleotide encoding the polypeptide comprising an amino acid sequence selected from the group consisting of SEQ ID NO:1–8, and fragments thereof. The invention also includes an isolated and purified polynucleotide variant having at least 90% polynucleotide sequence identity to the polynucleotide encoding the polypeptide comprising an amino acid sequence selected from the group consisting of SEQ ID NO:1–8, and fragments thereof.

Additionally, the invention provides an isolated and purified polynucleotide which hybridizes under stringent conditions to the polynucleotide encoding the polypeptide comprising an amino acid sequence selected from the group consisting of SEQ ID NO:1–8, and fragments thereof. The invention also provides an isolated and purified polynucleotide having a sequence which is complementary to the polynucleotide encoding the polypeptide comprising the amino acid sequence selected from the group consisting of SEQ ID NO:1–8, and fragments thereof.

The invention also provides an isolated and purified polynucleotide comprising a polynucleotide sequence selected from the group consisting of SEQ ID NO:9, SEQ ID NO:10, SEQ ID NO:11, SEQ ID NO:12, SEQ ID NO:13, SEQ ID NO:14, SEQ ID NO:15, SEQ ID NO:16 (SEQ ID NO:9–16), and fragments thereof. The invention further provides an isolated and purified polynucleotide variant having at least 90% polynucleotide sequence identity to the polynucleotide sequence selected from the group consisting of SEQ ID NO:9–6, and fragments thereof. The invention also provides an isolated and purified polynucleotide having a sequence which is complementary to the polynucleotide comprising a polynucleotide sequence selected from the group consisting of SEQ ID NO:9–16, and fragments thereof.

The invention also provides a method for detecting a polynucleotide in a sample containing nucleic acids, the method comprising the steps of (a) hybridizing the complement of the polynucleotide sequence to at least one of the polynucleotides of the sample, thereby forming a hybridization complex; and (b) detecting the hybridization complex, wherein the presence of the hybridization complex correlates with the presence of a polynucleotide in the sample. In one aspect, the method further comprises amplifying the polynucleotide prior to hybridization.

The invention further provides an expression vector containing at least a fragment of the polynucleotide encoding the polypeptide comprising an amino acid sequence selected from the group consisting of SEQ ID NO:1–8, and fragments thereof. In another aspect, the expression vector is contained within a host cell.

The invention also provides a method for producing a polypeptide, the method comprising the steps of: (a) culturing the host cell containing an expression vector containing at least a fragment of a polynucleotide under conditions suitable for the expression of the polypeptide; and (b) recovering the polypeptide from the host cell culture.

The invention also provides a pharmaceutical composition comprising a substantially purified polypeptide having the amino acid sequence selected from the group consisting of SEQ ID NO:1–8, and fragments thereof, in conjunction with a suitable pharmaceutical carrier.

The invention further includes a purified antibody which binds to a polypeptide selected from the group consisting of SEQ ID NO:1–8, and fragments thereof. The invention also provides a purified agonist and a purified antagonist to the polypeptide.

The invention also provides a method for treating or preventing a disorder associated with decreased expression or activity of PTAM, the method comprising administering to a subject in need of such treatment an effective amount of a pharmaceutical composition comprising a substantially purified polypeptide having the amino acid sequence selected from the group consisting of SEQ ID NO:1–8, and fragments thereof, in conjunction with a suitable pharmaceutical carrier.

The invention also provides a method for treating or preventing a disorder associated with increased expression or activity of PTAM, the method comprising administering to a subject in need of such treatment an effective amount of an antagonist of a polypeptide having an amino acid sequence selected from the group consisting of SEQ ID NO:1–8, and fragments thereof.

BRIEF DESCRIPTION OF THE TABLES

Table 1 shows nucleotide and polypeptide sequence identification numbers (SEQ ID NO), clone identification numbers (clone ID), cDNA libraries, and cDNA fragments used to assemble full-length sequences encoding PTAM.

Table 2 shows features of each polypeptide sequence including potential motifs, homologous sequences, and methods and algorithms used for identification of PTAM.

Table 3 shows the tissue-specific expression patterns of each nucleic acid sequence as determined by northern analysis, diseases or disorders associated with these tissues, and the vector into which each cDNA was cloned.

Table 4 describes the tissues used to construct the cDNA libraries from which Incyte cDNA clones encoding PTAM were isolated.

Table 5 shows the programs, their descriptions, references, and threshold parameters used to analyze PTAM.

DESCRIPTION OF THE INVENTION

Before the present proteins, nucleotide sequences, and methods are described, it is understood that this invention is not limited to the particular machines, materials and methods described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any machines, materials, and methods similar or equivalent to those described herein can be used to practice or test the present invention, the preferred machines, materials and methods are now described. All publications mentioned herein are cited for the purpose of describing and disclosing the cell lines, protocols, reagents and vectors which are reported in the publications and which might be used in connection with the invention. Nothing herein is to be construed as an admission that the invention is not entitled to antedate such disclosure by virtue of prior invention.

Definitions

"PTAM" refers to the amino acid sequences of substantially purified PTAM obtained from any species, particularly a mammalian species, including bovine, ovine, porcine, murine, equine, and preferably the human species, from any source, whether natural, synthetic, semi synthetic, or recombinant.

The term "agonist" refers to a molecule which, when bound to PTAM, increases or prolongs the duration of the effect of PTAM. Agonists may include proteins, nucleic acids, carbohydrates, or any other molecules which bind to and modulate the effect of PTAM.

An "allelic variant" is an alternative form of the gene encoding PTAM. Allelic variants may result from at least one mutation in the nucleic acid sequence and may result in altered mRNAs or in polypeptides whose structure or function may or may not be altered. Any given natural or recombinant gene may have none, one, or many allelic forms. Common mutational changes which give rise to allelic variants are generally ascribed to natural deletions, additions, or substitutions of nucleotides. Each of these types of changes may occur alone, or in combination with the others, one or more times in a given sequence.

"Altered" nucleic acid sequences encoding PTAM include those sequences with deletions, insertions, or substitutions of different nucleotides, resulting in a polynucleotide the same as PTAM or a polypeptide with at least one functional characteristic of PTAM. Included within this definition are polymorphisms which may or may not be readily detectable using a particular oligonucleotide probe of the polynucleotide encoding PTAM, and improper or unexpected hybridization to allelic variants, with a locus other than the normal chromosomal locus for the polynucleotide sequence encoding PTAM. The encoded protein may also be "altered," and may contain deletions, insertions, or substitutions of amino acid residues which produce a silent change and result in a functionally equivalent PTAM. Deliberate amino acid substitutions may be made on the basis of similarity in polarity, charge, solubility, hydrophobicity, hydrophilicity, and/or the amphipathic nature of the residues, as long as the biological or immunological activity of PTAM is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine.

The terms "amino acid" or "amino acid sequence" refer to an oligopeptide, peptide, polypeptide, or protein sequence, or a fragment of any of these, and to naturally occurring or synthetic molecules. In this context, "fragments," "immunogenic fragments," or "antigenic fragments" refer to fragments of PTAM which are preferably at least 5 to about 15 amino acids in length, most preferably at least 14 amino acids, and which retain some biological activity or immunological activity of PTAM. Where "amino acid sequence" is recited to refer to an amino acid sequence of a naturally occurring protein molecule, "amino acid sequence" and like terms are not meant to limit the amino acid sequence to the complete native amino acid sequence associated with the recited protein molecule.

"Amplification" relates to the production of additional copies of a nucleic acid sequence. Amplification is generally carried out using polymerase chain reaction (PCR) technologies well known in the art.

The term "antagonist" refers to a molecule which, when bound to PTAM, decreases the amount or the duration of the effect of the biological or immunological activity of PTAM. Antagonists may include proteins, nucleic acids, carbohydrates, antibodies, or any other molecules which decrease the effect of PTAM.

The term "antibody" refers to intact molecules as well as to fragments thereof, such as Fab, $F(ab')_2$, and Fv fragments, which are capable of binding the epitopic determinant. Antibodies that bind PTAM polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant" refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody.

The term "antisense" refers to any composition containing a nucleic acid sequence which is complementary to the "sense" strand of a specific nucleic acid sequence. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

The term "biologically active," refers to a protein having structural, regulatory, or biochemical functions of a naturally occurring molecule. Likewise, "immunologically active" refers to the capability of the natural, recombinant, or synthetic PTAM, or of any oligopeptide thereof, to induce a specific immune response in appropriate animals or cells and to bind with specific antibodies.

The terms "complementary" or "complementarity" refer to the natural binding of polynucleotides by base pairing. For example, the sequence "5' A-G-T 3'" bonds to the complementary sequence "3' T-C-A 5'." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands. This is of particular importance in amplification reactions, which depend upon binding between nucleic acids strands, and in the design and use of peptide nucleic acid (PNA) molecules.

A "composition comprising a given polynucleotide sequence" or a "composition comprising a given amino acid sequence" refer broadly to any composition containing the given polynucleotide or amino acid sequence. The composition may comprise a dry formulation or an aqueous solution. Compositions comprising polynucleotide sequences encoding PTAM or fragments of PTAM may be employed as hybridization probes. The probes may be stored in freezedried form and may be associated with a stabilizing agent such as a carbohydrate. In hybridizations, the probe may be deployed in an aqueous solution containing salts (e.g., NaCl), detergents (e.g., sodium dodecyl sulfate; SDS), and other components (e.g., Denhardt's solution, dry milk, salmon sperm DNA, etc.).

"Consensus sequence" refers to a nucleic acid sequence which has been resequenced to resolve uncalled bases, extended using XL-PCR kit (Perkin-Elmer, Norwalk CT) in the 5' and/or the 3' direction, and resequenced, or which has been assembled from the overlapping sequences of more than one Incyte Clone using a computer program for fragment assembly, such as the GELVIEW Fragment Assembly system (GCG, Madison Wis.). Some sequences have been both extended and assembled to produce the consensus sequence.

The term "correlates with expression of a polynucleotide" indicates that the detection of the presence of nucleic acids, the same or related to a nucleic acid sequence encoding PTAM, by northern analysis is indicative of the presence of nucleic acids encoding PTAM in a sample; and thereby correlates with expression of the transcript from the polynucleotide encoding PTAM.

A "deletion" refers to a change in the amino acid or nucleotide sequence that results in the absence of one or more amino acid residues or nucleotides.

The term "derivative" refers to the chemical modification of a polypeptide sequence, or a polynucleotide sequence. Chemical modifications of a polynucleotide sequence can include, for example, replacement of hydrogen by an alkyl, acyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

The term "similarity" refers to a degree of complementarity. There may be partial similarity or complete similarity. The word "identity" may substitute for the word "similarity." A partially complementary sequence that at least partially inhibits an identical sequence from hybridizing to a target nucleic acid is referred to as "substantially similar." The inhibition of hybridization of the completely complementary sequence to the target sequence may be examined using a hybridization assay (Southern or northern blot, solution hybridization, and the like) under conditions of reduced stringency. A substantially similar sequence or hybridization probe will compete for and inhibit the binding of a completely similar (identical) sequence to the target sequence under conditions of reduced stringency. This is not to say that conditions of reduced stringency are such that non-specific binding is permitted, as reduced stringency conditions require that the binding of two sequences to one another be a specific (i.e., a selective) interaction. The absence of non-specific binding may be tested by the use of a second target sequence which lacks even a partial degree of complementarity (e.g., less than about 30% similarity or identity). In the absence of non-specific binding, the substantially similar sequence or probe will not hybridize to the second non-complementary target sequence.

The phrases "percent identity" or "% identity" refer to the percentage of sequence similarity found in a comparison of two or more amino acid or nucleic acid sequences. Percent identity can be determined electronically, e.g., by using the MEGALIGN program (DNASTAR, Madison Wis.). The MEGALIGN program can create alignments between two or more sequences according to different methods, e.g., the clustal method. (See, e.g., Higgins, D. G. and P. M. Sharp (1988) Gene 73:237–244.) The clustal algorithm groups sequences into clusters by examining the distances between all pairs. The clusters are aligned pairwise and then in groups. The percentage similarity between two amino acid sequences, e.g., sequence A and sequence B; is calculated by dividing the length of sequence A, minus the number of gap residues in sequence A, minus the number of gap residues in sequence B, into the sum of the residue matches between sequence A and sequence B, times one hundred. Gaps of low or of no similarity between the two amino acid sequences are not included in determining percentage similarity. Percent identity between nucleic acid sequences can also be counted or calculated by other methods known in the art, e.g., the Jotun Hein method. (See, e.g., Hein, J. (1990) Methods Enzymol. 183:626–645.) Identity between sequences can also be determined by other methods known in the art, e.g., by varying hybridization conditions.

"Human artificial chromosomes" (HACs) are linear microchromosomes which may contain DNA sequences of about 6 kb to 10 Mb in size, and which contain all of the elements required for stable mitotic chromosome segregation and maintenance.

The term "humanized antibody" refers to antibody molecules in which the amino acid sequence in the non-antigen binding regions has been altered so that the antibody more closely resembles a human antibody, and still retains its original binding ability.

"Hybridization" refers to any process by which a strand of nucleic acid binds with a complementary strand through base pairing.

The term "hybridization complex" refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" or "addition" refer to changes in an amino acid or nucleotide sequence resulting in the addition of one or more amino acid residues or nucleotides, respectively, to the sequence found in the naturally occurring molecule.

"Immune response" can refer to conditions associated with inflammation, trauma, immune disorders, or infectious or genetic disease, etc. These conditions can be characterized by expression of various factors, e.g., cytokines, chemokines, and other signaling molecules, which may affect cellular and systemic defense systems.

The term "microarray" refers to an arrangement of distinct polynucleotides on a substrate.

The terms "element" or "array element" in a microarray context, refer to hybridizable polynucleotides arranged on the surface of a substrate.

The term "modulate" refers to a change in the activity of PTAM. For example, modulation may cause an increase or a decrease in protein activity, binding characteristics, or any other biological, functional, or immunological properties of PTAM.

The phrases "nucleic acid" or "nucleic acid sequence," as used herein, refer to a nucleotide, oligonucleotide, polynucleotide, or any fragment thereof. These phrases also refer to DNA or RNA of genomic or synthetic origin which may be single-stranded or double-stranded and may represent the sense or the antisense strand, to peptide nucleic acid (PNA), or to any DNA-like or RNA-like material. In this context, "fragments" refers to those nucleic acid sequences which comprise a region of unique polynucleotide sequence that specifically identifies SEQ ID NO:9–16, for example, as distinct from any other sequence in the same genome. For example, a fragment of SEQ ID NO:9–16 is useful in hybridization and amplification technologies and in analogous methods that distinguish SEQ ID NO:9–16 from related polynucleotide sequences. A fragment of SEQ ID NO:9–16 is at least about 15–20 nucleotides in length. The precise length of the fragment of SEQ ID NO:9–16 and the region of SEQ ID NO:9–16 to which the fragment corresponds are routinely determinable by one of ordinary skill in the art based on the intended purpose for the fragment. In some cases, a fragment, when translated, would produce polypeptides retaining some functional characteristic, e.g., antigenicity, or structural domain characteristic, e.g., ATP-binding site, of the full-length polypeptide.

The terms "operably associated" or "operably linked" refer to functionally related nucleic acid sequences. A promoter is operably associated or operably linked with a coding sequence if the promoter controls the translation of the encoded polypeptide. While operably associated or operably linked nucleic acid sequences can be contiguous and in the same reading frame, certain genetic elements, e.g., repressor genes, are not contiguously linked to the sequence encoding the polypeptide but still bind to operator sequences that control expression of the polypeptide.

The term "oligonucleotide" refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microarray. "Oligonucleotide" is substantially equivalent to the terms "amplimer," "primer," "oligomer," and "probe," as these terms are commonly defined in the art.

"Peptide nucleic acid" (PNA) refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA or RNA and stop transcript elongation, and may be pegylated to extend their lifespan in the cell.

The term "sample" is used in its broadest sense. A sample suspected of containing nucleic acids encoding PTAM, or fragments thereof, or PTAM itself, may comprise a bodily fluid; an extract from a cell, chromosome, organelle, or membrane isolated from a cell; a cell; genomic DNA, RNA, or cDNA, in solution or bound to a substrate; a tissue; a tissue print; etc.

The terms "specific binding" or "specifically binding" refer to that interaction between a protein or peptide and an agonist, an antibody, or an antagonist. The interaction is dependent upon the presence of a particular structure of the protein, e.g., the antigenic determinant or epitope, recognized by the binding molecule. For example, if an antibody is specific for epitope "A," the presence of a polypeptide containing the epitope A, or the presence of free unlabeled A, in a reaction containing free labeled A and the antibody will reduce the amount of labeled A that binds to the antibody.

The term "stringent conditions" refers to conditions which permit hybridization between polynucleotides and the claimed polynucleotides. Stringent conditions can be defined by salt concentration, the concentration of organic solvent, e.g., formamide, temperature, and other conditions well known in the art. In particular, stringency can be increased by reducing the concentration of salt, increasing the concentration of formamide, or raising the hybridization temperature.

The term "substantially purified" refers to nucleic acid or amino acid sequences that are removed from their natural environment and are isolated or separated, and are at least about 60% free, preferably about 75% free, and most preferably about 90% free from other components with which they are naturally associated.

A "substitution" refers to the replacement of one or more amino acids or nucleotides by different amino acids or nucleotides, respectively.

"Substrate" refers to any suitable rigid or semi-rigid support including membranes, filters, chips, slides, wafers, fibers, magnetic or nonmagnetic beads, gels, tubing, plates, polymers, microparticles and capillaries. The substrate can have a variety of surface forms, such as wells, trenches, pins, channels and pores, to which polynucleotides or polypeptides are bound.

"Transformation" describes a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment. The term "transformed" cells includes stably transformed cells in which the inserted DNA is capable of replication either as an autonomously replicating plasmid or as part of the host chromosome, as well as transiently transformed cells which express the inserted DNA or RNA for limited periods of time.

A "variant" of PTAM polypeptides refers to an amino acid sequence that is altered by one or more amino acid residues. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, LASERGENE software (DNASTAR).

The term "variant," when used in the context of a polynucleotide sequence, may encompass a polynucleotide sequence related to PTAM. This definition may also include, for example, "allelic" (as defined above), "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs) in which the polynucleotide sequence varies by one base. The presence of SNPs may be indicative of, for example, a certain population, a disease state, or a propensity for a disease state.

The Invention

The invention is based on the discovery of new human protein transport-associated molecules (PTAM), the polynucleotides encoding PTAM, and the use of these compositions for the diagnosis, treatment, or prevention of cell proliferative and secretory disorders.

Table 1 lists the Incyte Clones used to derive full length nucleotide sequences encoding PTAM. Columns 1 and 2 show the sequence identification numbers (SEQ ID NO) of the amino acid and nucleic acid sequences, respectively. Column 3 shows the Clone ID of the Incyte Clone in which nucleic acids encoding each PTAM were first identified, and column 4, the cDNA libraries from which these clones were isolated. Column 5 shows Incyte clones, their corresponding cDNA libraries, and shotgun sequences useful as fragments in hybridization technologies, and which are part of the consensus nucleotide sequence of each PTAM.

The columns of Table 2 show various properties of the polypeptides of the invention: column 1 references the SEQ ID NO; column 2 shows the number of amino acid residues in each polypeptide; column 3, potential phosphorylation sites; column 4, potential glycosylation sites; column 5, the amino acid residues comprising signature sequences and motifs; column 6, the identity of each protein; and column 7, analytical methods used to identify each protein through sequence homology and protein motifs.

The columns of Table 3 show the tissue-specificity and disease-association of nucleotide sequences encoding PTAM. The first column of Table 3 lists the polynucleotide sequence identifiers. The second column lists tissue categories which express PTAM as a fraction of total tissue categories expressing PTAM. The third column lists the disease classes associated with those tissues expressing PTAM. The fourth column lists the vectors used to subclone the cDNA library.

The following represent unique fragments of the nucleotide sequences encoding PTAM: the fragment of SEQ ID NO:9 from about nucleotide 1324 to about nucleotide 1422; the fragment of SEQ ID NO:10 from about nucleotide 455 to about nucleotide 499; the fragment of SEQ ID NO:11 from about nucleotide 101 to about nucleotide 145; the fragment of SEQ ID NO:12 from about nucleotide 178 to about nucleotide 240; the fragment of SEQ ID NO:13 from about nucleotide 543 to about nucleotide 590; the fragment of SEQ ID NO:14 from about nucleotide 525 to about nucleotide 584; the fragment of SEQ ID NO:15 from about nucleotide 371 to about nucleotide 433; and the fragment of SEQ ID NO:16 from about nucleotide 86 to about nucleotide 145.

The invention also encompasses PTAM variants. A preferred PTAM variant is one which has at least about 80%, more preferably at least about 90%, and most preferably at least about 95% amino acid sequence identity to the PTAM amino acid sequence, and which contains at least one functional or structural characteristic of PTAM.

The invention also encompasses polynucleotides which encode PTAM. In a particular embodiment, the invention encompasses a polynucleotide sequence comprising a sequence selected from the group consisting of SEQ ID NO:9–16, which encodes PTAM.

The invention also encompasses a variant of a polynucleotide sequence encoding PTAM. In particular, such a variant polynucleotide sequence will have at least about 70%, more preferably at least about 85%, and most preferably at least about 95% polynucleotide sequence identity to the polynucleotide sequence encoding PTAM. A particular aspect of the invention encompasses a variant of a polynucleotide sequence comprising a sequence selected from the group consisting of SEQ ID NO:9–16 which has at least about 70%, more preferably at least about 85%, and most preferably at least about 95% polynucleotide sequence identity to a nucleic acid sequence selected from the group consisting of SEQ ID NO:9–16. Any one of the polynucleotide variants described above can encode an amino acid sequence which contains at least one functional or structural characteristic of PTAM.

It will be appreciated by those skilled in the art that as a result of the degeneracy of the genetic code, a multitude of polynucleotide sequences encoding PTAM, some bearing minimal similarity to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring PTAM, and all such variations are to be considered as being specifically disclosed.

Although nucleotide sequences which encode PTAM and its variants are preferably capable of hybridizing to the nucleotide sequence of the naturally occurring PTAM under appropriately selected conditions of stringency, it may be advantageous to produce nucleotide sequences encoding PTAM or its derivatives possessing a substantially different codon usage, e.g., inclusion of non-naturally occurring codons. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding PTAM and its derivatives without altering the encoded amino acid sequences include the production of RNA transcripts having more desirable properties, such as a greater half-life, than transcripts produced from the naturally occurring sequence.

The invention also encompasses production of DNA sequences which encode PTAM and PTAM derivatives, or fragments thereof, entirely by synthetic chemistry. After production, the synthetic sequence may be inserted into any of the many available expression vectors and cell systems using reagents well known in the art. Moreover, synthetic chemistry may be used to introduce mutations into a sequence encoding PTAM or any fragment thereof.

Also encompassed by the invention are polynucleotide sequences that are capable of hybridizing to the claimed polynucleotide sequences, and, in particular, to those shown in SEQ ID NO:9–16 and fragments thereof under various conditions of stringency. (See, e.g., Wahl, G. M. and S. L. Berger (1987) Methods Enzymol. 152:399–407; Kimmel, A. R. (1987) Methods Enzymol. 152:507–511.) For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and most preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS); and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

The washing steps which follow hybridization can also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include temperature of at least about 25° C., more preferably of at least about 42° C., and most preferably of at least about 68° C. In a preferred embodiment, wash steps will occur at 25° C. in 30 mM NaCl, 3 mM trisodium citrate, and 0.1% SD S. In a more preferred embodiment, wash steps will occur at 42° C. in 15 mM NaCl, 1.5 mM trisodium citrate, and 0.1% SDS. In a most preferred embodiment, wash steps will occur at 68° C. in 15 mM NaCl, 1.5 mM trisodium citrate, and 0.1% SDS. Additional variations on these conditions will be readily apparent to those skilled in the art.

Methods for DNA sequencing are well known in the art and may be used to practice any of the embodiments of the invention. The methods may employ such enzymes as the Klenow fragment of DNA polymerase I, SEQUENASE (US Biochemical, Cleveland Ohio), TAQ polymerase (Perkin-Elmer), thermostable T7 polymerase (Amersham Pharmacia Biotech, Piscataway N.J.), or combinations of polymerases and proofreading exonucleases such as those found in the ELONGASE amplification system (Life Technologies, Gaithersburg Md.). Preferably, sequence preparation is automated with machines such as the Hamilton MICROLAB 2200 (Hamilton, Reno Nev.), PELTIER THERMAL CYCLER 200 (PTC200; MJ Research, Watertown Mass.) and the ABI CATALYST 800 PCR reaction machine (Perkin-Elmer). Sequencing is then carried out using either ABI 373 or 377 DNA Sequencing Systems (Perkin-Elmer) or the MEGABACE capillary electrophoresis system (Molecular Dynamics, Sunnyvale Calif.). The resulting sequences are analyzed using a variety of algorithms which are well known in the art. (See, e.g., Ausubel, F. M. (1997) *Short Protocols in Molecular Biology*, John Wiley & Sons, New York N.Y., unit 7.7; Meyers, R. A. (1995) *Molecular Biology and Biotechnology*, Wiley VCH, New York N.Y., pp. 856–853.)

The nucleic acid sequences encoding PTAM may be extended utilizing a partial nucleotide sequence and employing various PCR-based methods known in the art to detect upstream sequences, such as promoters and regulatory elements. For example, one method which may be employed, restriction-site PCR, uses universal and nested primers to amplify unknown sequence from genomic DNA within a cloning vector. (See, e.g., Sarkar, G. (1993) PCR Methods Applic. 2:318–322.) Another method, inverse PCR, uses primers that extend in divergent directions to amplify unknown sequence from a circularized template. The template is derived from restriction fragments comprising a known genomic locus and surrounding sequences. (See, e.g., Triglia, T. et al. (1988) Nucleic Acids Res. 16:8186.) A third method, capture PCR, involves PCR amplification of DNA fragments adjacent to known sequences in human and yeast artificial chromosome DNA. (See, e.g., Lagerstrom, M. et al. (1991) PCR Methods Applic. 111–119.) In this method, multiple restriction enzyme digestions and ligations may be used to insert an engineered double-stranded sequence into a region of unknown sequence before performing PCR. Other methods which may be used to retrieve unknown sequences are known in the art. (See, e.g., Parker, J. D. et al. (1991) Nucleic Acids Res. 19:3055–306.) Additionally, one may use PCR, nested primers, and PROMOTERFINDER libraries (Clontech, Palo Alto Calif.) to walk genomic DNA. This procedure avoids the need to screen libraries and is useful in finding intron/exon junctions. For all, PCR-based methods, primers may be designed using commercially available software, such as OLIGO 4.06 Primer Analysis software (National Biosciences, Plymouth Minn.) or another appropriate program, to be about 22 to 30 nucleotides in length, to have a GC content of about 50% or more, and to anneal to the template at temperatures of about 68° C. to 72° C.

When screening for full-length cDNAs, it is preferable to use libraries that have been size-selected to include larger cDNAs. In addition, random-primed libraries, which often include sequences containing the 5' regions of genes, are preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different nucleotide-specific, laser-stimulated fluorescent dyes, and a charge coupled device camera for detection of the emitted wavelengths. Output/light intensity may be converted to electrical signal using appropriate software (e.g., GENOTYPER and SEQUENCE NAVIGATOR, Perkin-Elmer), and the entire process from loading of samples to computer analysis and electronic data display may be computer controlled. Capillary electrophoresis is especially preferable for sequencing small DNA fragments which may be present in limited amounts in a particular sample.

In another embodiment of the invention, polynucleotide sequences or fragments thereof which encode PTAM may be cloned in recombinant DNA molecules that direct expression of PTAM, or fragments or functional equivalents thereof, in appropriate host cells. Due to the inherent degeneracy of the genetic code, other DNA sequences which encode substantially the same or a functionally equivalent amino acid sequence may be produced and used to express PTAM.

The nucleotide sequences of the present invention can be engineered using methods generally known in the art in order to alter PTAM-encoding sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth.

In another embodiment, sequences encoding PTAM may be synthesized, in whole or in part, using chemical methods well known in the art. (See, e.g., Caruthers, M. H. et al. (1980) Nucl. Acids Res. Symp. Ser. 215–223, and Horn, T. et al. (1980) Nucl. Acids Res. Symp. Ser. 225–232.) Alternatively, PTAM itself or a fragment thereof may be synthesized using chemical methods. For example, peptide synthesis can be performed using various solid-phase techniques. (See, e.g., Roberge, J. Y. et al. (1995) Science 269:202–204.) Automated synthesis may be achieved using the ABI 43 IA Peptide Synthesizer (Perkin-Elmer). Additionally, the amino acid sequence of PTAM, or any part thereof, may be altered during direct synthesis and/or combined with sequences from other proteins, or any part thereof, to produce a variant polypeptide.

The peptide may be substantially purified by preparative high performance liquid chromatography. (See, e.g, Chiez, R. M. and F. Z. Regnier (1990) Methods Enzymol. 182:392–421.) The composition of the synthetic peptides may be confirmed by amino acid analysis or by sequencing. (See, e.g., Creighton, T. (1984) *Proteins, Structures and Molecular Properties*, W. H. Freeman, New York N.Y.)

In order to express a biologically active PTAM, the nucleotide sequences encoding PTAM or derivatives thereof may be inserted into an appropriate expression vector, i.e., a vector which contains the necessary elements for transcriptional and translational control of the inserted coding sequence in a suitable host. These elements include regulatory sequences, such as enhancers, constitutive and inducible promoters, and 5' and 3' untranslated regions in the vector and in polynucleotide sequences encoding PTAM. Such elements may vary in their strength and specificity. Specific initiation signals may also be used to achieve more efficient translation of sequences encoding PTAM. Such signals include the ATG initiation codon and adjacent sequences, e.g. the Kozak sequence. In cases where sequences encoding PTAM and its initiation codon and upstream regulatory sequences are inserted into the appropriate expression vector, no additional transcriptional or translational control signals may be needed. However, in cases where only coding sequence, or a fragment thereof, is inserted, exogenous translational control signals including an in-frame ATG initiation codon should be provided by the vector. Exogenous translational elements and initiation codons may be of various origins, both natural and synthetic. The efficiency of expression may be enhanced by the inclusion of enhancers appropriate for the particular host cell system used. (See, e.g., Scharf, D. et al. (1994) Results Probl. Cell Differ. 20:125–162.)

Methods which are well known to those skilled in the art may be used to construct expression vectors containing sequences encoding PTAM and appropriate transcriptional and translational control elements. These methods include in vitro recombinant DNA techniques, synthetic techniques, and in vivo genetic recombination. (See, e.g., Sambrook, J. et al. (1989) *Molecular Cloning, A Laboratory Manual*, Cold Spring Harbor Press, Plainview N.Y., ch. 4, 8, and 16–17; Ausubel, F. M. et al. (1995) Current Protocols in Molecular Biology, John Wiley & Sons, New York N.Y., ch. 9, 13, and 16.)

A variety of expression vector/host systems may be utilized to contain and express sequences encoding PTAM. These include, but are not limited to, microorganisms such as bacteria transformed with recombinant bacteriophage, plasmid, or cosmid DNA expression vectors; yeast transformed with yeast expression vectors; insect cell systems infected with viral expression vectors (e.g., baculovirus); plant cell systems transformed with viral expression vectors (e.g., cauliflower mosaic virus, CaMV, or tobacco mosaic virus,TMV) or with bacterial expression vectors (e.g., Ti or pBR322 plasmids); or animal cell systems. The invention is not limited by the host cell employed.

In bacterial systems, a number of cloning and expression vectors may be selected depending upon the use intended for polynucleotide sequences encoding PTAM. For example, routine cloning, subcloning, and propagation of polynucleotide sequences encoding PTAM can be achieved using a multifunctional *E. coli* vector such as PBLUESCRIPT (Stratagene, La Jolla Calif.) or PSPORT1 plasmid (Life Technologies). Ligation of sequences encoding PTAM into the vector's multiple cloning site disrupts the lacZ gene, allowing a calorimetric screening procedure for identification of transformed bacteria containing recombinant molecules. In addition, these vectors may be useful for in vitro transcription, dideoxy sequencing, single strand rescue with helper phage, and creation of nested deletions in the cloned sequence. (See, e.g., Van Heeke, G. and S. M. Schuster (1989) J. Biol. Chem. 264:5503–5509.) When large quantities of PTAM are needed, e.g. for the production of antibodies, vectors which direct high level expression of PTAM may be used. For example, vectors containing the strong, inducible T5 or T7 bacteriophage promoter may be used.

Yeast expression systems may be used for production of PTAM. A number of vectors containing constitutive or inducible promoters, such as alpha factor, alcohol oxidase, and PGH, may be used in the yeast *Saccharomyces cerevisiae* or *Pichia pastoris*. In addition, such vectors direct either the secretion or intracellular retention of expressed proteins and enable integration of foreign sequences into the host genome for stable propagation. (See, e.g.; Ausubel, 1995, supra; Grant et al. (1987) Methods Enzymol. 153:516–54; and Scorer, C. A. et al. (1994) Bio/Technology 12:181–184.)

Plant systems may also be used for expression of PTAM. Transcription of sequences encoding PTAM may be driven viral promoters, e.g., the 35S and 19S promoters of CaMV used alone or in combination with the omega leader sequence from TMV. (Takamatsu, N. (1987) EMBO J. 6:307–311.) Alternatively, plant promoters such as the small subunit of RUBISCO or heat shock promoters may be used. (See, e.g., Coruzzi, G. et al. (1984) EMBO J. 3:1671–1680; Broglie, R. et al. (1984) Science 224:838–843; and Winter, J. et al. (1991) Results Probl. Cell Differ. 17:85–105.) These constructs can be introduced into plant cells by direct DNA transformation or pathogen-mediated transfection. (See, e.g., *The McGraw Hill Yearbook of Science and Technology* (1992) McGraw Hill; New York N.Y., pp. 191–196.)

In mammalian cells, a number of viral-based expression systems may be utilized. In cases where an adenovirus is used as an expression vector, sequences encoding PTAM may be ligated into an adenovirus transcription/translation complex consisting of the late promoter and tripartite leader sequence. Insertion in a non-essential E1 or E3 region of the viral genome may be used to obtain infective virus which expresses PTAM in host cells. (See, e.g., Logan, J. and T. Shenk (1984) Proc. Natl. Acad. Sci. 81:3655–3659.) In addition, transcription enhancers, such as the Rous sarcoma virus (RSV) enhancer, may be used to increase expression in mammalian host cells. SV40 or EBV-based vectors may also be used for high-level protein expression.

Human artificial chromosomes (HACs) may also be employed to deliver larger fragments of DNA than can be contained in and expressed from a plasmid. HACs of about 6 kb to 10 Mb are constructed and delivered via conventional delivery methods (liposomes, polycationic amino polymers, or vesicles) for therapeutic purposes. (See, e.g., Harrington, J. J. et al. (1997) Nat Genet. 15:345–355.)

For long term production of recombinant proteins in mammalian systems, stable expression of PTAM in cell lines is preferred. For example, sequences encoding PTAM can be transformed into cell lines using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to a selective agent, and its presence allows growth and recovery of cells which successfully express the introduced sequences. Resistant clones of stably transformed cells may be propagated using tissue culture techniques appropriate to the cell type.

Any number of selection systems may be used to recover transformed cell lines. These include, but are not limited to, the herpes simplex virus thymidine kinase and adenine phosphoribosyltransferase genes, for use in tk or apr cells, respectively. (See, e.g., Wigler, M. et al. (1977) Cell 11:223–232; Lowy, I. et al. (1980) Cell 22:817–823.) Also, antimetabolite, antibiotic, or herbicide resistance can be used as the basis for selection. For example, dhfr confers resistance to methotrexate; neo confers resistance to the aminoglycosides neomycin and G-418; and als or put confer resistance to chlorsulfuron and phosphinotricin acetyltransferase, respectively. (See, e.g., Wigler, M. et al. (1980) Proc. Natl. Acad. Sci. 77:3567–3570; Colbere-Garapin, F. et al. (1981) J. Mol. Biol. 150:1–14) Additional selectable genes have been described, e.g., trpB and hisD, which alter cellular requirements for metabolites. (See, e.g., Hartman, S. C. and R. C. Mulligan (1988) Proc. Natl. Acad. Sci. 85:8047–8051.) Visible markers, e.g., anthocyanins, green fluorescent proteins (GFP; Clontech), β glucuronidase and its substrate β-glucuronide, or luciferase and its substrate luciferin may be used. These markers can be used not only to identify transform ants, but also to quantify the amount of transient or stable protein expression attributable to a specific vector system. (See, e.g., Rhodes, C. A. (1995) Methods Mol. Biol. 55:121–131.)

Although the presence/absence of marker gene expression suggests that the gene of interest is also present, the presence and expression of the gene may need to be confirmed. For example, if the sequence encoding PTAM is inserted within a marker gene sequence, transformed cells containing sequences encoding PTAM can be identified by the absence of marker gene function. Alternatively, a marker gene can be placed in tandem with a sequence encoding PTAM under the control of a single promoter. Expression of the marker gene in response to induction or selection usually indicates expression of the tandem gene as well.

In general, host cells that contain the nucleic acid sequence encoding PTAM and that express PTAM may be identified by a variety of procedures known to those of skill in the art. These procedures include, but are not limited to, DNA-DNA or DNA-RNA hybridizations, PCR amplification, and protein bioassay or immunoassay techniques which include membrane, solution, or chip based technologies for the detection and/or quantification of nucleic acid or protein sequences.

Immunological methods for detecting and measuring the expression of PTAM using either specific polyclonal or monoclonal antibodies are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on PTAM is preferred, but a competitive binding assay may be employed. These and other assays are well known in the art. (See, e.g., Hampton, R. et al. (1990) *Serological Methods, a Laboratory Manual*, APS Press, St Paul Minn., Sect. IV; Coligan, J. E. et al. (1997) *Current Protocols in Immunology*, Greene Pub. Associates and Wiley-Interscience, New York N.Y.; and Pound, J. D. (1998) *Immunochemical Protocols*, Humana Press, Totowa N. J.).

A wide variety of labels and conjugation techniques are known by those skilled in the art and may be used in various nucleic acid and amino acid assays. Means for producing labeled hybridization or PCR probes for detecting sequences related to polynucleotides encoding PTAM include oligolabeling, nick translation, end-labeling, or PCR amplification using a labeled nucleotide. Alternatively, the sequences encoding PTAM, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Amersham Pharmacia Biotech, Promega (Madison Wis.), and US Biochemical. Suitable reporter molecules or labels which may be used for ease of detection include radionuclides; enzymes, fluorescent, chemiluminescent, or chromogenic agents, as well as substrates, cofactors, inhibitors, magnetic particles, and the like.

Host cells transformed with nucleotide sequences encoding PTAM may be cultured under conditions suitable for the expression and recovery of the protein from cell culture. The protein produced by a transformed cell may be secreted or retained intracellularly depending on the sequence and/or the vector used. As will be understood by those of skill in the art, expression vectors containing polynucleotides which encode PTAM may be designed to contain signal sequences which direct secretion of PTAM through a prokaryotic or eukaryotic cell membrane.

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to specify protein targeting, folding, and/or activity. Different host cells which have specific cellular machinery and characteristic mechanisms for post-translational activities (e.g., CHO, HeLa, MDCK, HEK293, and W138), are available from the American Type Culture Collection (ATCC, Bethesda Md.) and may be chosen to ensure the correct modification and processing of the foreign protein.

In another embodiment of the invention, natural, modified, or recombinant nucleic acid, sequences encoding PTAM may be ligated to a heterologous sequence resulting in translation of a fusion protein in any of the aforementioned host systems. For example, a chimeric PTAM protein containing a heterologous moiety that can be recognized by a commercially available antibody may facilitate the screening of peptide libraries for inhibitors of PTAM activity. Heterologous protein and peptide moieties may also facilitate purification of fusion proteins using commercially available affinity matrices. Such moieties include, but are not limited to, glutathione S-transferase (GST), maltose binding protein (MBP), thioredoxin (Trx), calmodulin binding peptide (CBP), 6-His, FLAG, c-myc, and hemagglutinin (HA). GST, MBP, Trx, CBP, and 6-His enable purification of their cognate fusion proteins on immobilized glutathione, maltose, phenylarsine oxide, calmodulin, and metal-chelate resins, respectively. FLAG, c-myc, and hemagglutinin (HA) enable immunoaffinity purification of fusion proteins using commercially available monoclonal and polyclonal antibodies that specifically recognize these epitope tags. A fusion protein may also be-engineered to contain a proteolytic cleavage site located between the PTAM encoding sequence and the heterologous protein sequence, so that PTAM may be cleaved away from the heterologous moiety following purification. Methods for fusion protein expression and purification are discussed in Ausubel (1995, supra, ch 10.) A variety of commercially available kits may also be used to facilitate expression and purification of fusion proteins.

In a further embodiment of the invention, synthesis of radiolabeled PTAM may be achieved in vitro using the TNT rabbit reticulocyte lysate or wheat germ extract systems (Promega). These systems couple transcription and translation of protein-coding sequences operably associated with the T7, T3, or SP6 promoters. Translation takes place in the presence of a radiolabeled amino acid precursor, preferably $^{35}$S-methionine.

Fragments of PTAM may be produced not only by recombinant production, but also by direct peptide synthesis using solid-phase techniques. (See, e.g., Creighton, supra pp. 55–60.) Protein synthesis may be performed by manual techniques or by automation. Automated synthesis may be achieved, for example, using the ABI 431 A Peptide Synthesizer (Perkin-Elmer). Various fragments of PTAM may be synthesized separately and then combined to produce the full length molecule.

Therapeutics

Chemical and structural similarity, e.g., in the context of sequences and motifs, exists between PTAM and protein transport-associated molecules. In addition, the expression of PTAM is closely associated with cell proliferation. Therefore, in cell proliferative and secretory disorders where the expression or activity of PTAM is low, it is desirable to increase the expression or activity of PTAM. In cell proliferative and secretory disorders where the expression or activity of PTAM is high, it is desirable to decrease the expression or activity of PTAM.

Therefore, in one embodiment, PTAM or a fragment or derivative thereof may be administered to a subject to treat or prevent a disorder associated with cell proliferation or secretion in which the expression or activity of PTAM is decreased. Examples of such disorders include, but are not limited to, cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, *thymus*, thyroid, and uterus; immune disorders such as actinic keratosis, acquired immunodeficiency syndrome (AIDS), Addison's disease, adult respiratory distress syndrome, allergies, ankylosing spondylitis, amyloidosis, anemia, arteriosclerosis, asthma, atherosclerosis, autoimmune hemolytic anemia, autoimmune thyroiditis, bronchitis, bursitis, cholecystitis, cirrhosis, contact dermatitis, Crohn's disease, atopic dermatitis, dermatomyositis, diabetes mellitus, emphysema, erythroblastosis fetalis, erythema nodosum, atrophic gastritis, glomerulonephritis, Goodpasture's syndrome, gout, Graves' disease, Hashimoto's thyroiditis, paroxysmal nocturnal hemoglobinuria, hepatitis, hypereosinophilia, irritable bowel syndrome, episodic lymphopenia with lymphocytotoxins, mixed connective tissue disease (MCTD), multiple sclerosis, myasthenia gravis, myocardial or pericardial inflammation, myelofibrosis, osteoarthritis, osteoporosis, pancreatitis, polycythemia vera, polymyositis, psoriasis, Reiter's syndrome, rheumatoid arthritis, scleroderma, Sjögren's syndrome, systemic anaphylaxis, systemic lupus erythematosus, systemic sclerosis, primary thrombocythemia, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma; and secretory disorders such as cystic fibrosis, glucose-galactose malabsorption syndrome, hypercholesterolemia, diabetes insipidus, hyper- and hypoglycemia, goiter, Cushing's disease, and other conditions associated with abnormal vesicle trafficking, such as allergies, including hay fever, asthma, and urticaria (hives), autoimmune hemolytic anemia, Chediak-Higashi syndrome, and toxic shock syndrome.

In another embodiment, a vector capable of expressing PTAM or a fragment or derivative thereof may be administered to a subject to treat or prevent a disorder including, but not limited to, those described above.

In a further embodiment, a pharmaceutical composition comprising a substantially purified PTAM in conjunction with a suitable pharmaceutical carrier may be administered to a subject to treat or prevent a disorder including, but not limited to, those provided above.

In still another embodiment, an agonist which modulates the activity of PTAM may be administered to a subject to treat or prevent a disorder including, but not limited to, those listed above.

In a further embodiment, an antagonist of PTAM may be administered to a subject to treat or prevent a disorder in which the expression or activity of PTAM is increased. Examples of such disorders include, but are not limited to, those described above. In one aspect, an antibody which specifically binds PTAM may be used directly as an antagonist or indirectly as a targeting or delivery mechanism for bringing a pharmaceutical agent to cells or tissue which express PTAM.

In an additional embodiment, a vector expressing the complement of the polynucleotide encoding PTAM may be administered to a subject to treat or prevent a disorder including, but not limited to, those described above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of PTAM may be produced using methods which are generally known in the art. In particular, purified PTAM may be used to produce antibodies or to screen libraries of pharmaceutical agents to identify those which specifically bind PTAM. Antibodies to PTAM may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

For the production of antibodies, various hosts including goats, rabbits, rats, mice, humans, and others may be immunized by injection with PTAM or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to PTAM have an amino acid sequence consisting of at least about 5 amino acids, and, more preferably, of at least about 10 amino acids. It is also preferable that these oligopeptides, peptides, or fragments are identical to a portion of the amino acid sequence of the natural protein and contain the entire amino acid sequence of a small, naturally occurring molecule. Short stretches of PTAM amino acids may be fused with those of another protein, such as KLH, and antibodies to the chimeric molecule may be produced.

Monoclonal antibodies to PTAM may be prepared using any technique which provides for the production of antibody molecules by continuous cell lines in culture. These include, but are not limited to, the hybridoma technique, the human B-cell hybridoma technique, and the EBV-hybridoma technique. (See, e.g., Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; and Cole, S. P. et al. (1984) Mol. Cell Biol. 62:109–120.)

In addition, techniques developed for the production of "chimeric antibodies." such as the splicing of mouse antibody genes to human antibody genes to obtain a molecule with appropriate antigen specificity and biological activity, can be used. (See, e.g., Morrison, S. L. et al. (1984) Proc. Natl. Acad. Sci. 81 6851–6855; Neuberger, M. S. et al. (1984) Nature 312:604–608; and Takeda, S. et al. (1985) Nature 314:452–454.) Alternatively, techniques described for the production of single chain antibodies may be adapted, using methods known in the art, to produce PTAM-specific single chain antibodies. Antibodies with related specificity, but of distinct idiotypic composition, may be generated by chain shuffling from random combinatorial immunoglobulin libraries. (See, e.g., Burton D. R. (1991) Proc. Natl. Acad. Sci. 88:10134–10137.)

Antibodies may also be produced by inducing in vivo production in the lymphocyte population or by screening immunoglobulin libraries or panels of highly specific binding reagents as disclosed in the literature. (See, e.g., Orlandi, R. et al. (1989) Proc. Natl. Acad. Sci. 86: 3833–3837; Winter, G. et al. (1991) Nature 349:293–299.)

Antibody fragments which contain specific binding sites for PTAM may also be generated. For example, such fragments include, but are not limited to, F(ab')$_2$ fragments produced by pepsin digestion of the antibody molecule and Fab fragments generated by reducing the disulfide bridges of the F(ab')$_2$ fragments. Alternatively, Fab expression libraries may be constructed to allow rapid and easy identification of monoclonal Fab fragments with the desired specificity. (See, e.g., Huse, W. D. et al. (1989) Science 246:1275–1281.)

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between PTAM and its specific antibody. A two-site, monoclonal-based immunoassay utilizing monoclonal antibodies reactive to two non-interfering PTAM epitopes is preferred, but a competitive binding assay may also be employed (Pound, supra.)

In another embodiment of the invention, the polynucleotides encoding PTAM, or any fragment or complement thereof, may be used for therapeutic purposes. In one aspect, the complement of the polynucleotide encoding PTAM may be used in situations in which it would be desirable to block the transcription of the mRNA. In particular, cells may be transformed with sequences complementary to polynucleotides encoding PTAM. Thus, complementary molecules or fragments may be used to modulate PTAM activity, or to achieve regulation of gene function. Such technology is now well known in the art, and sense or antisense oligonucleotides or larger fragments can be designed from various locations along the coding or control regions of sequences encoding PTAM.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors to express nucleic acid sequences complementary to the polynucleotides encoding PTAM. (See; e.g., Sambrook, supra; Ausubel, 1995, supra.)

Genes encoding PTAM can be turned off by transforming a cell or tissue with expression vectors which express high levels of a polynucleotide, or fragment thereof, encoding PTAM. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding PTAM. Oligonucleotides derived from the transcription initiation site, e.g., between about positions −10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee, J. E. et al. (1994) in Huber, B. E. and B. I. Carr, *Molecular and Immunologic Approaches*, Futura Publishing, Mt. Kisco N.Y., pp. 163–177.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of sequences encoding PTAM.

Specific ribozyme cleavage sites within any potential RNA target are initially identified by scanning the target molecule for ribozyme cleavage sites, including the following-sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding PTAM. Such DNA sequences may be incorporated into a wide variety of vectors with suitable RNA polymerase promoters such as T7 or SP6. Alternatively, these cDNA constructs that synthesize complementary RNA, constitutively or inducibly, can be introduced into cell lines, cells, or tissues.

RNA molecules may be modified to increase intracellular stability and half-life. Possible modifications include, but are riot limited to, the addition of flanking sequences at the 5' and/or 3' ends of the molecule, or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (See e.g., Goldman, C. K. et al. (0.1997) Nature Biotechnology 15:462–466.)

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical or sterile composition, in conjunction with a pharmaceutically acceptable carrier, for any of the therapeutic effects discussed above. Such pharmaceutical compositions may consist of PTAM, antibodies to PTAM, and mimetics, agonists, antagonists, or inhibitors of PTAM. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs, or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing, Easton Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol; Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds maybe prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acid. Salts tend to be more soluble in aqueous or other protonic solvents than are the corresponding free base forms. In other cases, the preferred preparation may be a lyophilized powder which may contain any or all of the following: 1 mM to 50 mM histidine, 0.1% to 2% sucrose, and 2% to 7% mannitol, at a pH range of 4.5 to 5.5, that is combined with buffer prior to use.

After pharmaceutical compositions have been prepared, they can be placed in an appropriate container and labeled for treatment of an indicated condition. For administration of PTAM, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells or in animal models such as mice, rats, rabbits, dogs, or pigs. An animal model may also be used to determine the appropriate concentration range and route of administration. Such information can then be used to determine useful doses and routes for administration in humans.

A therapeutically effective dose refers to that amount of active ingredient, for example PTAM or fragments thereof, antibodies of PTAM, and agonists, antagonists or inhibitors of PTAM, which ameliorates the symptoms or condition. Therapeutic efficacy and toxicity may be determined by standard pharmaceutical procedures in cell cultures or with experimental animals, such as by calculating the $ED_{50}$ (the dose therapeutically effective in 50% of the population) or $LD_{50}$ (the dose lethal to 50% of the population) statistics. The dose ratio of therapeutic to toxic effects is the therapeutic index, and it can be expressed as the $ED_{50}/LD_{50}$. Ratio. Pharmaceutical compositions which exhibit large therapeutic indices are preferred. The data obtained from cell culture assays and animal studies are used to formulate a range of dosage for human use. The dosage contained in such compositions is preferably within a range of circulating concentrations that includes the $ED_{50}$ with little or no toxicity. The dosage varies within this range depending upon the dosage form employed, the sensitivity of the patient, and the route of administration.

The exact dosage will be determined by the practitioner, in light of factors related to the subject requiring treatment.

Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

Normal dosage amounts may vary from about 0.1 $\mu$g to 100,000 $\mu$g, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind PTAM may be used for the diagnosis of cell proliferative and secretory disorders characterized by expression of PTAM; or in assays to monitor patients being treated with PTAM or agonists, antagonists, or inhibitors of PTAM. Antibodies useful for diagnostic purposes may be prepared in the same manner as described above for therapeutics, Diagnostic assays for PTAM include methods which utilize the antibody and a label to detect PTAM in human body fluids or in extracts of cells or tissues. The antibodies may be used with or without modification, and may be labeled by covalent or non-covalent attachment of a reporter molecule. A wide variety of reporter molecules, several of which are described above, are known in the art and may be used.

A variety of protocols for measuring PTAM, including ELISAs, RIAs, and FACS, are known in the art and provide a basis for diagnosing altered or abnormal levels of PTAM expression. Normal or standard values for PTAM expression are established by combining body fluids or cell extracts taken from normal mammalian subjects, preferably human, with antibody to PTAM under conditions suitable for complex formation. The amount of standard complex formation may be quantitated by various methods, preferably by photometric means. Quantities of PTAM expressed in subject, control, and disease samples from biopsied tissues are compared with the standard values. Deviation between standard and subject values establishes the parameters for diagnosing disease.

In another embodiment of the invention, the polynucleotides encoding PTAM may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of PTAM may be correlated with disease. The diagnostic assay may be used to determine absence, presence, and excess expression of PTAM, and to monitor regulation of PTAM levels during therapeutic intervention.

In one aspect, hybridization with PCR probes which are capable of detecting polynucleotide sequences, including genomic sequences, encoding PTAM or closely related molecules may be used to identify nucleic acid sequences which encode PTAM. The specificity of the probe, whether it is made from a highly specific region, e.g., the 5' regulatory region, or from a less specific region, e.g., a conserved motif, and the stringency of the hybridization or amplification (maximal, high, intermediate, or low), will determine whether the probe identifies only naturally occurring sequences encoding PTAM, allelic variants, or related sequences.

Probes may also be used for the detection of related sequences, and should preferably have at least 50% sequence identity to any of the PTAM encoding sequences. The hybridization probes of the subject invention may be DNA or RNA and may be derived from the sequence of SEQ ID NO:9–16 or from genomic sequences including promoters, enhancers, and introns of the PTAM gene.

Means for producing specific hybridization probes for DNAs encoding PTAM include the cloning of polynucleotide sequences encoding PTAM or PTAM derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}P$ or $^{32}S$, or by enzymatic labels, such as alkaline phosphatase coupled to the probe via avidin/biotin coupling systems, and the like.

Polynucleotide sequences encoding PTAM may be used for the diagnosis of cell proliferative and secretory disorders associated with expression of PTAM. Examples of such disorders include, but are not limited to, cell proliferative disorders such as cancers, including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, *thymus*, thyroid, and uterus; immune disorders such as actinic keratosis, acquired immunodeficiency syndrome (AIDS), Addison's disease, adult respiratory distress syndrome, allergies, ankylosing spondylitis, amyloidosis, anemia, arteriosclerosis, asthma, atherosclerosis, autoimmune hemolytic anemia, autoimmune thyroiditis, bronchitis, bursitis, cholecystitis, cirrhosis, contact dermatitis, Crohn's disease, atopic dermatitis, dermatomyositis, diabetes mellitus, emphysema, erythroblastosis fetalis, erythema nodosum, atrophic gastritis, glomerulonephritis, Goodpasture's syndrome, gout, Graves' disease, Hashimoto's thyroiditis, paroxysmal nocturnal hemoglobinuria, hepatitis, hypereosinophilia, irritable bowel syndrome, episodic lymphopenia with lymphocylotoxins, mixed connective tissue disease (MCTD), multiple sclerosis, myasthenia gravis, myocardial or pericardial inflammation, myelofibrosis, osteoarthritis, osteoporosis, pancreatitis, polycythemia vera, polymyositis, psoriasis, Reiter's syndrome, rheumatoid arthritis, scleroderma, Sjögren's syndrome, systemic anaphylaxis, systemic lupus erythematosus, systemic sclerosis, primary thrombocythemia, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma; and secretory disorders such as cystic fibrosis, glucose-galactose malabsorption syndrome, hypercholesterolemia, diabetes insipidus, hyper- and hypoglycemia, goiter, Cushing's disease, and other conditions associated with abnormal vesicle trafficking, such as allergies, including hay fever, asthma, and urticaria (hives), autoimmune hemolytic anemia, Chediak-Higashi syndrome, and toxic shock syndrome. The polynucleotide sequences encoding PTAM may be used in Southern or northern analysis, dot blot, or other membrane-based technologies; in PCR technologies: in dipstick, pin, and ELISA assays; and in microarrays utilizing fluids or tissues from patients to detect altered PTAM expression. Such qualitative or quantitative methods are well known in the art.

In a particular aspect, the nucleotide sequences encoding PTAM may be useful in assays that detect the presence of associated disorders, particularly those mentioned above. The nucleotide sequences encoding PTAM may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered in comparison to a control sample then the presence of altered levels of nucleotide sequences encoding PTAM in the sample indicates the presence of the associated disorder: Such assays may also be used to evaluate the efficacy of a particular therapeutic treatment regimen in animal studies, in clinical trials, or to monitor the treatment of an individual patient.

In order to provide a basis for the diagnosis of a disorder associated with expression of PTAM, a normal or standard profile for expression is established. This may be accomplished by combining body fluids or cell extracts taken from normal subjects, either animal or human, with a sequence, or a fragment thereof, encoding PTAM, under conditions suitable for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period ranging from several days to months.

With respect to cancer, the presence of an abnormal amount of transcript (either under- or over-expressed) in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding PTAM may involve the use of PCR. These oligomers may be chemically synthesized, generated enzymatically, or produced in vitro. Oligomers will preferably contain a fragment of a polynucleotide encoding PTAM, or a fragment of a polynucleotide complementary to the polynucleotide encoding PTAM, and will be employed under optimized conditions for identification of a specific gene or condition. Oligomers may also be employed under less stringent conditions for detection or quantitation of closely related DNA or RNA sequences.

Methods which may also be used to quantitate the expression of PTAM include radiolabeling or biotinylating nucleotides, coamplification of a control nucleic acid, and interpolating results from standard curves. (See, e.g., Melby, P. C. et al. (1993) J. Immunol. Methods 159:235–244;

Duplaa, C. et al. (1993) Anal. Biochem. 229–236.) The speed of quantitation of multiple samples may be accelerated by running the assay in an ELISA format where the oligomer of interest is presented in various dilutions and a spectrophotometric or colorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents.

Microarrays may be prepared, used, and analyzed using methods known in the art. (See, e.g., Brennan, T. M. et al. (1995) U.S. Pat. No. 5,474,796; Schena, M. et al. (1996) Proc. Natl. Acad. Sci. 93:10614–10619; Baldeschweiler et al. (1995) PCT application WO95/251116; Shalon, D. et al. (1995) PCT application WO95/35505; Heller, R. A. et al. (1997) Proc. Natl. Acad. Sci. 94:2150–2155; and Heller, M. J. et al. (1997) U.S. Pat. No. 5,605,662.)

In another embodiment of the invention, nucleic acid sequences encoding PTAM may be used to generate hybridization probes useful in mapping the naturally occurring genomic sequence. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome cDNA libraries. (See, e.g., Harrington, J. J. et al. (1997) Nat Genet. 15:345–355; Price, C. M. (1993) Blood Rev. 7:127–134; and Trask, B. J. (1991) Trends Genet. 7:149–154.)

Fluorescent in situ hybridization (FISH) may be correlated with other physical chromosome mapping techniques and genetic map data. (See, e.g., Heinz-Ulrich, et at. (1995) in Meyers, supra, pp. 965–968.) Examples of genetic map data can be found in various scientific journals or at the Online Mendelian Inheritance in Man (OMIM) site. Correlation between the location of the gene encoding PTAM on a physical chromosomal map and a specific disorder, or a predisposition to a specific disorder, may help define the region of DNA associated with that disorder. The nucleotide sequences of the invention may be used to detect differences in gene sequences among normal, carrier, and affected individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms by physical mapping. This provides valuable information to investigators searching for disease genes using positional cloning or other gene discovery techniques. Once the disease or syndrome has been crudely localized by genetic linkage to a particular genomic region, e.g., ataxia-telangiectasia to 11q22-23, any sequences mapping to that area may represent associated or regulatory genes for further investigation. (See, e.g., Gatti, R. A. et al. (1988) Nature 336:577–580.). The nucleotide sequence of the subject invention may also be used to detect differences in the chromosomal location due to translocation, inversion, etc., among normal, carrier, or affected individuals.

In another embodiment of the invention, PTAM, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between PTAM and the agent being tested may be measured.

Another technique for drug screening provides for high throughput screening of compounds having suitable binding affinity to the protein of interest. (See, e.g., Geysen, et al. (1984) PCT application WO84103564.) In this method, large numbers of different small test compounds are synthesized on a solid substrate. The test compounds are reacted with PTAM, or fragments thereof, and washed. Bound PTAM is then detected by methods well known in the art. Purified PTAM can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding PTAM specifically compete with a test compound for binding PTAM. In this manner, antibodies can be used to detect the presence of any peptide which shares one or more antigenic determinants with PTAM.

In additional embodiments, the nucleotide sequences which encode PTAM may be used in any molecular biology techniques that have yet id be developed, provided the new techniques rely on properties of nucleotide sequences that are currently known, including, but not limited to, such properties as the triplet genetic code and specific base pair interactions.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

The disclosures of all patents, applications, and publications mentioned above and below, in particular U.S. Ser. No. 60/098,206, are hereby expressly incorporated by reference.

EXAMPLES

I. Construction of cDNA Libraries

RNA was purchased from Clontech or isolated from tissues described in Table 4. Some tissues were homogenized and lysed in guanidinium isothiocyanate, while others were homogenized and lysed in phenol or in a suitable mixture of denaturants, such as TRIZOL (Life Technologies), a monophasic solution of phenol and guanidine isothiocyanate. The resulting lysates were centrifuged over CsCl cushions or extracted with chloroform. RNA was precipitated from the lysates with either isopropanol or sodium acetate and ethanol, or by other routine methods.

Phenol extraction and precipitation of RNA were repeated as necessary to increase RNA purity. In some cases, RNA was treated with DNase. For most libraries, poly(A+) RNA was isolated using oligo d(T)-coupled paramagnetic particles (Promega), OLIGOTEX latex particles (QIAGEN, Valencia Calif.), or an OLIGOTEX mRNA purification kit (QIAGEN). Alternatively, RNA was isolated directly from tissue lysates using other RNA isolation kits, e.g., the POLY(A)PURE mRNA purification kit (Ambion, Austin Tex.).

In some cases, Stratagene was provided with RNA and constructed the corresponding cDNA libraries. Otherwise, cDNA was synthesized and cDNA libraries were constructed with the UNIZAP vector system (Stratagene) or SUPERSCRIPT plasmid system (Life Technologies), using the recommended procedures or similar methods known in the art. (See, e.g., Ausubel, 1997, supra, units 5.1–6.6.) Reverse transcription was initiated using oligo d(T) or random primers. Synthetic oligonucleotide adapters were ligated to double stranded cDNA, and the cDNA was digested with the appropriate restriction enzyme or enzymes. For most libraries, the cDNA was size-selected (300–1000 bp) using SEPHACRYL S1000, SEPHAROSE CL2B, or SEPHAROSE CL4B column chromatography (Amersham Pharmacia Biotech) or preparative agarose gel electrophoresis. cDNAs were ligated into compatible restriction enzyme sites of the polylinker of a suitable plasmid, e.g., PBLUESCRIPT plasmid (Stratagene), PSPORT1 plasmid (Life Technologies), or pINCY (Incyte Pharmaceuticals, Palo Alto Calif.). Recombinant plasmids were transformed into competent *E. coli* cells including XL1-Blue, XL1-BlueMRF, or SOLR from Stratagene or DH5α, DH 10B, or ElectroMAX DH10B from Life Technologies.

II. Isolation of cDNA Clones

Plasmids were recovered from host cells by in vivo excision, using the UNIZAP vector system (Stratagene) or cell lysis. Plasmids were purified using at least one of the following: a MAGIC or WIZARD Minipreps DNA purification system (Promega); an AGTC Miniprep purification kit (Edge Biosystems, Gaithersburg Md.); and QIAWELL 8 Plasmid, QIAWELL 8 Plus Plasmid, QIAWELL 8 Ultra Plasmid purification systems or the REAL Prep 96 plasmid kit from QIAGEN. Following precipitation, plasmids were resuspended in 0.11 ml of distilled water and stored, with or without lyophilization, at 4° C.

Alternatively, plasmid DNA was amplified from host cell lysates using direct link PCR in a high-throughput format (Rao, V. B. (11994) Anal. Biochem. 216:1–14.) Host cell lysis and thermal cycling steps were carried out in a single reaction mixture. Samples were processed and stored in 384-well plates, and the concentration of amplified plasmid DNA was quantified fluorometrically using PICOGREEN dye (Molecular Probes, Eugene Oreg.) and a Fluoroskan II fluorescence scanner (Labsystems Oy, Helsinki, Finland).

III. Sequencing and Analysis

The cDNAs were prepared for sequencing using the ABI CATALYST 800 (Perkin-Elmer) or the HYDRA microdispenser (Robbins Scientific, Sunnyvale Calif.) or MICROLAB 2200 (Hamilton, Reno Nev.) systems in combination with the PTC-200 thermal cyclers (MJ Research, Watertown Mass.). The cDNAs were sequenced using the ABI PRISM 373 or 377 sequencing systems (Perkin-Elmer) and standard ABI protocols, base calling software, and kits. In one alternative, cDNAs were sequenced using the MEGABACE 1000 capillary electrophoresis sequencing system (Molecular Dynamics, Sunnyvale Calif.). In another alternative, the cDNAs were amplified and sequenced using the ABI PRISM BIGDYE Terminator cycle sequencing ready reaction kit (Perkin-Elmer). In yet another alternative, cDNAs were sequenced using solutions dyes from Amersham Pharmacia Biotech. Reading frames for the ESTs were determined using standard methods (reviewed in Ausubel, 1997, supra, unit 7.7.) Some of the cDNA sequences were selected for extension using the techniques disclosed in Example V.

The polynucleotide sequences derived from cDNA, extension, and shotgun sequencing were assembled and analyzed using a combination of software programs which utilize algorithms well known to those skilled in the art. Table 5 summarizes the software programs, descriptions, references, and threshold parameters used. The first column of Table 5 shows the tools, programs, and algorithms used, the second column provides a brief description thereof, the third column presents the references which are incorporated by reference herein, and the fourth column presents, where applicable, the scores, probability values, and other parameters used to evaluate the strength of a match between two sequences (the higher the probability the greater the homology). Sequences were analyzed using MACDNASIS PRO software (Hitachi Software Engineering, S. San Francisco Calif.) and LASERGENE software (DNASTAR).

The polynucleotide sequences were validated by removing vector, linker, and polyA sequences and by masking ambiguous bases, using algorithms and programs based on BLAST, dynamic programing, and dinucleotide nearest neighbor analysis. The sequences were then queried against a selection of public databases such as GenBank primate, rodent, mammalian, vertebrate, and eukaryote databases, and BLOCKS to acquire annotation, using programs based on BLAST, FASTA, and BLIMPS. The sequences were assembled into full length polynucleotide sequences using programs based on Phred, Phrap, and Consed, and were screened for open reading frames using programs based on GeneMark, BLAST, and FASTA. The full length polynucleotide sequences were translated to derive the corresponding full length amino acid sequences, and these full length sequences were subsequently analyzed by querying against databases such as the GenBank databases (described above), SwissProt, BLOCKS, PRINTS, PFAM, and Prosite.

The programs described above for the assembly and analysis of full length polynucleotide and amino acid sequences were also used to identify polynucleotide sequence fragments from SEQ ID NO:8–14. Fragments from about 20 to about 4000 nucleotides which are useful in hybridization and amplification technologies were described in The Invention section above.

IV. Northern Analysis

Northern analysis is a laboratory technique used to detect the presence of a transcript of a gene and involves the hybridization of a labeled nucleotide sequence to a membrane on which RNAs from a particular cell type or tissue have been bound. (See, e.g., Sambrook, supra, ch. 7; Ausubel, 1995, supra, ch. 4 and 16.)

Analogous computer techniques applying BLAST were used to search for identical or related molecules in nucleotide databases such as GenBank or LIFESEQ database (Incyte Pharmaceuticals). This analysis is much faster than multiple membrane-based hybridizations. In addition, the sensitivity of the computer search can be modified to determine whether any particular match is categorized as exact or similar. The basis of the search is the product score, which is defined as:

$$\frac{\% \text{ sequence identity} \times \% \text{ maximum } BLAST \text{ score}}{100}$$

The product score takes into account both the degree of similarity between two sequences and the length of the sequence match. For example, with a product score of 40, the match will be exact within a 1% to 2% error, and, with a product score of 70, the match will be exact. Similar molecules are usually identified by selecting those which show product scores between 15 and 40, although lower scores may identify related molecules.

The results of northern analyses are reported as a list of libraries in which the transcript encoding PTAM occurred. Abundance and percent abundance are also reported. Abundance directly reflects the number of times a particular transcript is represented in a cDNA library, and percent abundance is abundance divided by the total number of sequences examined in the cDNA library. Further analyses produced the percentage values of tissue-specific and disease expression which are reported in Table 3.

V. Extension of PTAM Encoding Polynucleotides

The nucleic acid sequences of Incyte ESTs 12033, 1209687, 1717058, 1749964, 1856357, 1871275, 2645806, and 3437773 were used to design oligonucleotide primers for extending partial nucleotide sequence to full length. For each nucleic acid sequence, one primer was synthesized to initiate extension of an antisense polynucleotide, and the other was synthesized to initiate extension of a sense polynucleotide. Primers were used to facilitate the extension of the known sequence "outward" which generates amplicons containing new unknown nucleotide sequence for the region of interest. The initial primers were designed from the cDNA using OLIGO 4.06 software (National Biosciences), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human cDNA libraries (Life Technologies) were used to extend the sequence. If more than one extension is necessary or desired, additional sets of primers are designed to further extend the known region.

High fidelity amplification was obtained by following the instructions for the XL-PCR kit (Perkin-Elmer) and thoroughly mixing the enzyme and reaction mix. PCR was performed using the PTC200 thermal cycler (M. J. Research) beginning with 40 pmol of each primer and the recommended concentrations of all other components of the kit, with the following parameters:

| Step 1  | 94° C. for 1 min (initial denaturation) |
| Step 2  | 65° C. for 1 min |
| Step 3  | 68° C. for 6 min |
| Step 4  | 94° C. for 15 sec |
| Step 5  | 65° C. for 1 min |
| Step 6  | 68° C. for 7 min |
| Step 7  | Repeat steps 4–6 for an additional 15 cycles |
| Step 8  | 94° C. for 15 sec |
| Step 9  | 65° C. for 1 min |
| Step 10 | 68° C. for 7:15 min |
| Step 11 | Repeat steps 8–10 for an additional 12 cycles |
| Step 12 | 72° C. for 8 min |
| Step 13 | 4° C. (and holding) |

A 5 µl to 10 µl aliquot of the reaction mixture was analyzed by electrophoresis on a low concentration (about 0.6% to 0.8%) agarose mini-gel to determine which reactions were successful in extending the sequence. Bands thought to contain the largest products were excised from the gel, purified using the QIAQUICK kit (QIAGEN), and trimmed of overhangs using Klenow enzyme to facilitate religation and cloning.

After ethanol precipitation, the products were redissolved in 13 µl of ligation buffer, 1 µl T4-DNA ligase (15 units) and 1 µl T4 polynucleotide kinase were added, and the mixture was incubated at room temperature for 2 to 3 hours, or overnight at 16° C. Competent E. coli cells (in 40 µu of appropriate media) were transformed with 3 µl of ligation mixture and cultured in 80 µl of SOC medium. (See, e.g., Sambrook, supra, Appendix A, p. 2.) After incubation for one hour at 37° C., the E. coli mixture was plated on Luria Bertani (LB) agar (See, e.g., Sambrook, supra, Appendix A, p. 1) containing carbenicillin (2×carb). The following day, several colonies were randomly picked from each plate and cultured in 150 µl of liquid LB/2×carb medium placed in an individual well of an appropriate commercially-available sterile 96-well microtiter plate. The following day, 5 µl of each overnight culture was transferred into a non-sterile 96-well plate and, after dilution 1:10 with water, 5 µl from each sample was transferred into a PCR array.

For PCR amplification, 18 µl of concentrated PCR reaction mix (3.3×) containing 4 units of rTth DNA polymerase, a vector primer, and one or both of the gene specific primers used for the extension reaction were added to each well. Amplification was performed using the following conditions:

| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequences of SEQ ID NO:9–16 are used to obtain 5' regulatory sequences using the procedure above, oligonucleotides designed for 5' extension, and an appropriate genomic library.

VI. Labeling and Use of Individual Hybridization Probes

Hybridization probes derived from SEQ ID NO:9–16 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO 4.06 software (National Biosciences) and labeled by combining 50 pmol of each oligomer, 250 µci of [$\gamma$-$^{32}$P] adenosine triphosphate (Amersham Pharmacia Biotech), and T4 polynucleotide kinase (DuPont NEN, Boston Mass.). The labeled oligonucleotides are substantially purified using a SEPHADEX G-25 superfine size exclusion dextran bead column (Amersham Pharmacia Biotech). An aliquot containing $10^7$ counts per minute of the labeled probe is used in a typical membrane-based hybridization analysis of human genomic DNA digested with one of the following endonucleases: Ase I, Bgl II, Eco RI, Pst I, XbaI, or Pvu II (DuPont NEN).

The DNA from each digest is fractionated on a 0.7% agarose gel and transferred to NYTRAN PLUS, nylon membranes (Schleicher & Schuell, Durham N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT-AR film (Eastman Kodak, Rochester N.Y.) is exposed to the blots to film for several hours, hybridization patterns are compared visually.

VII. Microarrays

A chemical coupling procedure and an ink jet device can be used to synthesize array elements on the surface of a substrate. (See, e.g., Baldeschweiler, supra.) An array analogous to a dot or slot blot may also be used to arrange and link elements to the surface of a substrate using thermal, UV, chemical, or mechanical bonding procedures. A typical array may be produced by hand or using available methods and machines and contain any appropriate number of elements. After hybridization, nonhybridized probes are removed and a scanner used to determine the levels and patterns of fluorescence. The degree of complementarity and the relative abundance of each probe which hybridizes to an element on the microarray may be assessed through analysis of the scanned images.

Full-length cDNAs, Expressed Sequence Tags (ESTs), or fragments thereof may comprise the elements of the microarray. Fragments suitable for hybridization can be selected using software well known in the art such as LASERGENE software (DNASTAR). Full-length cDNAs, ESTs, or fragments thereof corresponding to one of the nucleotide sequences of the present invention, or selected at random from a cDNA library relevant to the present invention, are arranged on an appropriate substrate, e.g., a glass slide. The cDNA is fixed to the slide using, e.g., UV cross-linking followed by thermal and chemical treatments and subsequent drying. (See, e.g., Schena, M. et al. (1995) Science 270:467–470; Shalon, D. et al. (1996) Genome Res. 6:639–645.) Fluorescent probes are prepared and used for hybridization to the elements on the substrate. The substrate is analyzed by procedures described above.

VIII. Complementary Polynucleotides

Sequences complementary to the PTAM-encoding sequences, or any parts thereof, are used to detect, decrease, or inhibit expression of naturally occurring PTAM. Although use of oligonucleotides comprising from about 15 to 30 base pairs is described, essentially the same procedure is used with smaller or with larger sequence fragments. Appropriate oligonucleotides are designed using OLIGO 4.06 software (National Biosciences) and the coding sequence of PTAM. To inhibit transcription, a complementary oligonucleotide is designed from the most unique 5' sequence and used to prevent promoter binding to the coding sequence. To inhibit translation, a complementary oligonucleotide is designed to prevent ribosomal binding to the PTAM-encoding transcript.

Ix. Expression of PTAM

Expression and purification of PTAM is achieved using bacterial or virus-based expression systems. For expression of PTAM in bacteria, cDNA is subcloned into an appropriate vector containing an antibiotic resistance gene and an inducible promoter that directs high levels of cDNA transcription. Examples of such promoters include, but are not limited to, the trp-lac (tac) hybrid promoter and the T5 or T7 bacteriophage promoter in conjunction with the lac operator regulatory element. Recombinant vectors are transformed into suitable bacterial hosts, e.g., BL21(DE3). Antibiotic resistant bacteria express PTAM upon induction with isopropyl beta-D-thiogalactopyranoside (IPTG). Expression of PTAM in eukaryotic cells is achieved by infecting insect or mammalian cell lines with recombinant *Autographica californica* nuclear polyhedrosis virus (AcMNPV), commonly known as baculovirus. The nonessential polyhedrin gene of baculovirus is replaced with cDNA encoding PTAM by either homologous recombination or bacterial-mediated transposition involving transfer plasmid intermediates. Viral infectivity is maintained and the strong polyhedrin promoter drives high levels of cDNA transcription. Recombinant baculovirus is used to infect *Spodoptera frugiperda* (Sf9) insect cells in most cases, or human hepatocytes, in some cases. Infection of the latter requires additional genetic modifications to baculovirus. (See Engelhard, E. K. et al. (1994). Proc. Natl. Acad. Sci. USA 91:3224–3227; Sandig, V. et al. (1996) Hum. Gene Ther. 7:1937–1945.)

In most expression systems, PTAM is synthesized as a fusion protein with, e.g., glutathione S-transferase (GST) or a peptide epitope tag, such as FLAG or 6-His, permitting rapid, single-step, affinity-based purification of recombinant fusion protein from crude cell lysates. GST, a 26-kilodalton enzyme from *Schistosoma japonicum*, enables the purification of fusion proteins on immobilized glutathione under conditions that maintain protein activity and antigenicity (Amersham Pharmacia Biotech) Following purification, the GST moiety can be proteolytically cleaved from PTAM at specifically engineered sites. FLAG, an 8-amino acid peptide, enables immunoaffinity purification using commercially available monoclonal and polyclonal anti-FLAG antibodies (Eastman Kodak). 6-His, a stretch of six consecutive histidine residues, enables purification on metal-chelate resins (QIAGEN). Methods for protein expression and purification are discussed in Ausubel (1995, supra, ch 10 and 16.) Purified PTAM obtained by these methods can be used directly in the following activity assay.

X. Functional Assays

PTAM function is assessed by expressing the sequences encoding PTAM at physiologically elevated levels in mammalian cell culture systems. cDNA is subcloned into a mammalian expression vector containing a strong promoter that drives high levels of cDNA expression. Vectors of choice include pCMV SPORT (Life Technologies) and pCR3.1 (Invitrogen, Carlsbad Calif.), both of which contain the cytomegalovirus promoter. 5–10 $\mu$g of recombinant vector are transiently transfected into a human cell line, preferably of endothelial or hematopoietic origin, using either liposome formulations or electroporation. 1–2 $\mu$g of an additional plasmid containing sequences encoding a marker protein are co-transfected. Expression of a marker protein provides a means to distinguish transfected cells from nontransfected cells and is a reliable predictor of cDNA expression from the recombinant vector. Marker proteins of choice include, e.g., Green Fluorescent Protein (GFP; Clontech), CD64, or a CD64-GFP fusion protein. Flow cytometry (FCM), an automated, laser optics-based technique, is used to identify transfected cells expressing GFP or CD64-GFP, and to evaluate properties, for example; their apoptotic state. FCM detects and quantifies the uptake of fluorescent molecules that diagnose events preceding or coincident with cell death. These events include changes in nuclear DNA content as measured by staining of DNA with propidium iodide; changes in cell size and granularity as measured by forward light scatter and 90 degree side light scatter; down-regulation of DNA synthesis as measured by decrease in bromodeoxyuridine uptake; alterations in expression of cell surface and intracellular proteins as measured by reactivity with specific antibodies; and alterations in plasma membrane composition as measured by the binding of fluorescein-conjugated Annexin V protein to the cell surface. Methods in flow cytometry are discussed in Ormerod, M. G. (1994) *Flow Cytometry*, Oxford, New York N.Y.

The influence of PTAM on gene expression can be assessed using highly purified populations of cells transfected with sequences encoding PTAM and either CD64 or CD64-GFP. CD64 and CD64-GFP are expressed on the surface of transfected cells and bind to conserved regions of human immunoglobulin G (IgG). Transfected cells are efficiently separated from nontransfected cells using magnetic beads coated with either human IgG or antibody against CD64 (DYNAL, Lake Success N.Y.). mRNA can be purified from the cells using methods well known by those of skill in the art. Expression of mRNA encoding PTAM and other genes of interest can be analyzed by northern analysis or microarray techniques.

XI. Production of PTAM Specific Antibodies

PTAM substantially purified using polyacrylamide gel electrophoresis (PAGE; see, e.g., Harrington, M. G. (1990) Methods Enzymol. 182:488–495), or other purification techniques, is used to immunize rabbits and to produce antibodies using standard protocols.

Alternatively, the PTAM amino acid sequence is analyzed using LASERGENE software (DNASTAR) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art. (See, e.g., Ausubel, 1995, supra, ch. 11.)

Typically, oligopeptides 15 residues in length are synthesized using an ABI 431 A Peptide Synthesizer (Perkin-Elmer) using fmoc-chemistry and coupled to KLH (Sigma-Aldrich, St. Louis Mo.) by reaction with N-maleimidobenzoyl-N-hydroxysuccinimide ester (MBS) to increase immunogenicity. (See, e.g., Ausubel, 1995, supra.) Rabbits are immunized with the oligopeptide-KLH complex in complete Freund's adjuvant. Resulting antisera are tested for antipeptide activity by, for example, binding the peptide to plastic, blocking with 1% BSA, reacting with rabbit antisera, washing, and reacting with radio-iodinated goat anti-rabbit IgG.

XII. Purification of Naturally Occurring PTAM Using Specific Antibodies

Naturally occurring or recombinant PTAM is substantially purified by immunoaffinity chromatography using antibodies specific for PTAM. An immunoaffinity column is constructed by covalently coupling anti-PTAM antibody to an activated chromatographic resin, such as CNBr-activated SEPHAROSE (Amersham Pharmacia Biotech). After the coupling, the resin is blocked and washed according to the manufacturer's instructions.

Media containing PTAM are passed over the immunoaffinity column, and the column is washed under conditions that allow the preferential absorbance of PTAM (e.g., high ionic strength buffers in the presence of detergent). The column is eluted under conditions that disrupt antibody/PTAM binding (e.g., a buffer of pH 2 to pH 3, or a high concentration of a chaotrope, such as urea or thiocyanate ion), and PTAM is collected.

XIII. Identification of Molecules Which Interact with PTAM

PTAM, or biologically active fragments thereof, are labeled with 125I Bolton-Hunter reagent. (See, e.g., Bolton et al. (1973) Biochem. J. 133:529.) Candidate molecules previously arrayed in the wells of a multi-well plate are incubated with the labeled PTAM, washed, and any wells with labeled PTAM complex are assayed. Data obtained using different concentrations of PTAM are used to calculate values for the number, affinity, and association of PTAM with the candidate molecules.

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

TABLE 1

| Protein SEQ ID NO: | Nucleotide SEQ ID NO: | Clone ID | Library | Fragments |
| --- | --- | --- | --- | --- |
| 1 | 9 | 012033 | THP1PLB01 | 012033H1 (THP1PLB01), 3714OH1 (LUNGNOT02), 1835003T6 (BRAINON01), 2184660T6 (SININOT01), 2355213F6 and 2355213T6 (LUNGNOT20), 3564476H1 (SKINNOT05) |
| 2 | 10 | 1209687 | BRSTNOT02 | 1209687H1 (BRSTNOT02), 1212604T6 (BRSTTUT01), 2702873H1 (OVARTUT10) |
| 3 | 11 | 1717058 | UCMCNOT02 | 015033F1 and 015033R1 (HUVELPB01), 04185IR1 (TBLYNOT01), 625952H1 (PGANNOT01), 1580781H1 (DUODNOT01), 1717058F6 and 1717058H1 (UCMCNOT02) |
| 4 | 12 | 1749964 | STOMTUT02 | 455769F1 and 455769R1 (KERANOT01), 734407R1 (TONSNOT01), 1688918F6 (PROSTUT10), 1749964H1 (STOMTUT02), 1867108F6 (SKINBIT01), 1917583H1 (PROSNOT06), 1920136R6 (BRSTTUT01), 2683294F6 (SINIUCT01) |
| 5 | 13 | 1856357 | PROSNOT18 | 1610265F6 (COLNTUT06), 618761H1 (PGANNOT01), 732969R1 (LUNGNOT03), 874322H1 (LUNGAST01), 968936H1 (BRSTNOT05), 1394835F6 (THYRNOT03), 1856357F6 and 1856357H1 (PROSNOT18), 2788175H1 (BRSTNOT16), 2870537H1 (THYRNOT10), 3359258H1 (PROSTUT16), 3931139H1 (PROSTUT09) |
| 6 | 14 | 1871275 | SKINBIT01 | 081150F1 (SYNORAB01), 1509160F1 (LUNGNOT14), 1553311F1 (BLADTUT04), 1871275H1 (SKINBIT01), SBAA02579F1 |
| 7 | 15 | 2645806 | OVARTUT04 | 2239005F6 (PANCTUT02), 3598925H1 (DRGTNOT01), 2645806F6 and 2645806H1 (OVARTUT04) |
| 8 | 16 | 3437773 | PENCNOT05 | 148721F1 (FIBRNGT01), 1291051F6 (BRAINOT11), 1979290R6 (LUNGTUT03), 2203762F6 (SPLNFET02), 3437773H1 (PENCNOT05) |

TABLE 2

| Protein Seq ID NO: | Amino Acid Residues | Potential Phosphorylation Sites | Potential Glycosylation Sites | Signature Sequence | Identification | Analytical Methods |
|---|---|---|---|---|---|---|
| 1 | 480 | S56 T62 S70 T76 S84 T90 S98 S112 T118 S126 T132 S140 T146 S154 T160 S168 T174 S182 T188 S196 T202 S210 T216 S224 S238 T244 S258 S298 T331 T358 T363 S365 S25 S47 S53 S95 T104 T109 T123 T137 S193 S221 T422 | N39 N82 N96 N152 N180 N208 N222 N373 N377 | M1-P19 F385-A402 | human TGN38 homolog hTGN51 | BLAST SPScan HMM |
| 2 | 140 | T8 T26 S53 S57 S73 S98 | | | nuclear transport factor NTF2 | BLAST |
| 3 | 519 | S185 T16 S33 S40 S127 S147 S174 S227 T165 S179 T246 T296 T470 | N300 | K181-Y198 | sorting nexin 2 | PRINTS BLAST |
| 4 | 613 | S233 S37 S39 S73 T84 S183 T286 T287 S327 S115 T124 S225 S229 S435 S480 S541 S551 | | | novel VHS domain containing protein | BLAST |
| 5 | 719 | S27 S78 T137 S243 S257 S413 T432 T443 S654 S174 T234 S304 S316 S357 T575 S630 S700 T716 Y397 Y600 | | | hook2 protein | BLAST |
| 6 | 175 | S72 S101 T145 T171 S89 S139 T162 | | G2 | TCR delta | MOTIFS BLAST |
| 7 | 142 | T3 T9 S54 T99 | N123 | | nuclear transport factor NTF2 | BLAST |
| 8 | 248 | T126 T167 T54 T91 S228 | N73 | G50-S57 K45-C248 | Ras family member Rab4b | MOTIFS PFAM BLAST PRINTS |

TABLE 3

| Polynucleotide Seq ID NO: | Tissue Expression (Fraction of Total) | Disease Class (Fraction of Total) | Vector |
|---|---|---|---|
| 9 | Hematopoietic/Immune (0.314) Reproductive (0.171) Gastrointestinal (0.143) | Proliferative (0.571) Inflammation (0.485) | PBLUESCRIPT |
| 10 | Reproductive (0.500) Cardiovascular (0.143) Hematopoietic/Immune (0.143) | Proliferative (0.643) Inflammation (0.429) | PSPORT1 |
| 11 | Reproductive (0.256) Hematopoietic/Immune (0.174) Nervous (0.163) | Proliferative (0.651) Inflammation (0.279) | pINCY |
| 12 | Reproductive (0.245) Hematopoietic/Immune (0.147) Nervous (0.127) | Proliferative (0.687) Inflammation (0.284) | pINCY |
| 13 | Reproductive (0.435) Gastrointestinal (0.130) Nervous (0.101) | Proliferative (0.826) Inflammation (0.217) | pINCY |
| 14 | Cardiovascular (0.233) Musculoskeletal (0.233) Gastrointestinal (0.140) | Inflammation (0.535) Cancer (0.395) | pINCY |
| 15 | Cardiovascular (0.308) Reproductive (0.231) Nervous (0.154) Gastrointestinal (0.154) | Proliferative (0.846) Inflammation (0.308) | pINCY |
| 16 | Nervous (0.245) Hematopoietic/Immune (0.184) Cardiovascular (0.163) | Cancer (0.449) Inflammation (0.367) | pINCY |

TABLE 4

| Polynucleotide SEQ ID NO: | Clone ID | Library | Library Description |
|---|---|---|---|
| 9 | 012033 | THP1PLB01 | Library was constructed using RNA isolated from THP-1 cells cultured for 48 hours with 100 ng/ml phorbol ester (PMA), followed by a 4-hour culture in media containing 1 ug/ml LPS. THP-1 (ATCC TIB 202) is a human promonocyte line derived from the peripheral blood of a 1-year-old male with acute monocytic leukemia (ref: Int. J. Cancer (1980) 26:171). |
| 10 | 1209687 | BRSTNOT02 | Library was constructed using RNA isolated from diseased breast tissue removed from a 55-year-old Caucasian female during a unilateral extended simple mastectomy. Pathology indicated proliferative fibrocysytic changes characterized by apocrine metaplasia, sclerosing adenosis, cyst formation, and ductal hyperplasia without atypia. Pathology for the associated tumor tissue indicated an invasive grade 4 mammary adenocarcinoma. Patient history included atrial tachycardia and a benign neoplasm. Family history included cardiovascular and cerebrovascular disease. |
| 11 | 1717058 | UCMCNOT02 | Library was constructed using RNA isolated from mononuclear cells obtained from the umbilical cord blood of nine individuals. |
| 12 | 1749964 | STOMTUT02 | Library was constructed using RNA isolated from stomach tumor tissue obtained from a 68-year-old Caucasian female during a partial gastrectomy. Pathology indicated a malignant lymphoma of diffuse large-cell type. Previous surgeries included cholecystectomy. Patient history included thalassemia. Family history included acute leukemia, atherosclerotic coronary artery disease, and malignant neoplasm of the esophagus and stomach. |
| 13 | 1856357 | PROSNOT18 | Library was constructed using RNA isolated from diseased prostate tissue removed from a 58-year-old Caucasian male during a radical cystectomy, radical prostatectomy, and gastrostomy. Pathology indicated adenofibromatous hyperplasia; this tissue was associated with a grade 3 transitional cell carcinoma. Patient history included angina and emphysema. Family history included acute myocardial infarction, atherosclerotic coronary artery disease, and type II diabetes. |
| 14 | 1871275 | SKINBIT01 | Library was constructed using RNA isolated from diseased skin tissue of the left lower leg. Patient history included erythema nodosum of the left lower leg. |
| 15 | 2645806 | OVARTUT04 | Library was constructed using RNA isolated from ovarian tumor tissue removed from a 53-year-old Caucasian female during a total abdominal hysterectomy, removal of the fallopian tubes and ovaries, regional lymph node excision, and peritoneal tissue destruction. Pathology indicated grade 1 transitional cell carcinoma of the right ovary. The left ovary had a hemorrhagic corpus luteum. The uterus had multiple leiomyomas (1 submucosal, 11 intramural), and the endometrium was inactive. The cul-de-sac contained abundant histiocytes and rare clusters of mesothelial cells. Patient history included breast fibrosclerosis and chronic stomach ulcer. Family history included acute stomach ulcer with perforation, breast cancer, bladder cancer, rectal/anal cancer, benign hypertension, coronary angioplasty, and hyperlipidemia. |
| 16 | 3437773 | PENCNOT05 | Library was constructed using RNA isolated from penis left corpus cavernosum tissue removed from a male. |

TABLE 5

| Program | Description | Reference | Parameter Threshold |
|---|---|---|---|
| ABI FACTURA | A program that removes vector sequences and masks ambiguous bases in nucleic acid sequences. | Perkin-Elmer Applied Biosystems, Foster City, CA. | |
| ABI/ PARACEL FDF | A Fast Data Finder useful in comparing and annotating amino acid or nucleic acid sequences. | Perkin-Elmer Applied Biosystems, Foster City, CA; Paracel Inc., Pasadena, CA. | Mismatch <50% |
| ABI AutoAssembler | A program that assembles nucleic acid sequences. | Perkin-Elmer Applied Biosystems, Foster City, CA. | |
| BLAST | A Basic Local Alignment Search Tool useful in sequence similarity search for amino acid and nucleic acid sequences. BLAST includes five functions: blastp, blastn, blastx, tblastn, and tblastx. | Altschul, S. F. et al. (1990) J. Mol. Biol. 215:403–410; Altschul, S. F. et al. (1997) Nucleic Acids Res. 25:3389–3402. | ESTs: Probability value = 1.0E-8 or less Full Length sequences: Probability value = 1.0E-10 or less |
| FASTA | A Pearson and Lipman algorithm that searches for similarity between a query sequence and a group of sequences of the same type. FASTA comprises as least five functions: fasta, tfasta, fastx, tfastx, and ssearch. | Pearson, W. R. and D. J. Lipman (1988) Proc. Natl. Acad Sci. 85:2444–2448; Pearson, W. R. (1990) Methods Enzymol. 183:63–98; and Smith, T. F. and M. S. Waterman (1981) Adv. Appl. Math. 2:482–489. | ESTs: fasta E value = 1.06E-6 Assembled ESTs: fasta Identity = 95% or greater and Match length = 200 bases or greater; fastx E value = 1.0E-8 or less |

TABLE 5-continued

| Program | Description | Reference | Parameter Threshold |
|---|---|---|---|
| BLIMPS | A BLocks IMProved Searcher that matches a sequence against those in BLOCKS and PRINTS databases to search for gene families, sequence homology, and structural fingerprint regions. | Henikoff, S. and J. G. Henikoff, Nucl. Acid Res., 19:6565–72, 1991. J. G. Henikoff and S. Henikoff (1996) Methods Enzymol. 266:88–105; and Attwood, T. K. et al. (1997) J. Chem. Inf. Comput. Sci. 37:417–424. | Full Length sequences: fastx score = 100 or greater Score = 1000 or greater; Ratio of Score/Strength = 0.75 or larger; and Probability value = 1.0E-3 or less |
| PFAM | A Hidden Markov Models-based application useful for protein family search. | Krogh, A. et al. (1994) J. Mol. Biol., 235:1501–1531; Sonnhammer, E. L. L. et al. (1988) Nucleic Acids Res. 26:320–322. | Score = 10–50 bits, depending on individual protein families |
| ProfileScan | An algorithm that searches for structural and sequence motifs in protein sequences that match sequence patterns defined in Prosite. | Gribskov, M. et al. (1988) CABIOS 4:61–66; Gribskov, et al. (1989) Methods Enzymol. 183:146–159; Bairoch, A. et al. (1997) Nucleic Acids Res. 25:217–221. | Score = 4.0 or greater |
| Phred | A base-calling algorithm that examines automated sequencer traces with high sensitivity and probability. | Ewing, B. et al. (1998) Genome Res. 8:175–185; Ewing, B. and P. Green (1998) Genome Res. 8:186–194. | |
| Phrap | A Phils Revised Assembly Program including SWAT and CrossMatch, programs based on efficient implementation of the Smith-Waterman algorithm, useful in searching sequence homology and assembling DNA sequences. | Smith, T. F. and M. S. Waterman (1981) Adv. Appl. Math. 2:482–489; Smith, T. F. and M. S. Waterman (1981) J. Mol. Biol. 147:195–197; and Green, P., University of Washington, Seattle, WA. | Score = 120 or greater; Match length = 56 or greater |
| Consed | A graphical tool for viewing and editing Phrap assemblies | Gordon, D. et al. (1998) Genome Res. 8:195–202. | |
| SPScan | A weight matrix analysis program that scans protein sequences for the presence of secretory signal peptides. | Nielson, H. et al. (1997) Protein Engineering 10:1–6; Claverie, J. M. and S. Audie (1997) CABIOS 12:431–439. | Score = 5 or greater |
| Motifs | A program that searches amino acid sequences for patterns that matched those defined in Prosite. | Bairoch et al. supra; Wisconsin Package Program Manual, version 9, page M51–59, Genetics Computer Group, Madison, WI. | |

What is claimed is:

1. An isolated polynucleotide encoding a polypeptide selected from the group consisting of:
   a) a polypeptide comprising an amino acid sequence of SEQ ID NO: 2, SEQ ID NO: 3, SEQ ID NO: 5, SEQ ID NO: 7 or SEQ ID NO: 8, and
   b) a polypeptide comprising an amino acid sequence at least 90% identical to an amino acid sequence of SEQ ID NO: 2, SEQ ID NO: 7 or SEQ ID NO: 8.

2. A recombinant polynucleotide comprising a promoter sequence operably linked to the polynucleotide of claim 1.

3. A cell transformed with the recombinant polynucleotide of claim 2.

4. A method of producing a polypeptide selected from the group consisting of: a) a polypeptide comprising an amino acid sequence of SEQ ID NO: 2, SEQ ID NO: 3, SEQ ID NO: 5, SEQ ID NO: 7 or SEQ ID NO: 8, and b) a polypeptide comprising an amino acid sequence at least 90% identical to an amino acid sequence of SEQ ID NO: 2, SEQ ID NO: 7 or SEQ ID NO: 8, the method comprising:
   i) culturing a cell under conditions suitable for expression of the polypeptide, wherein said cell is transformed with the polynucleotide of claim 1 operably linked to a promoter sequence, and
   ii) recovering the polypeptide so expressed.

5. An isolated polynucleotide selected from the group consisting of:
   a) a polynucleotide comprising a polynucleotide sequence of SEQ ID NO: 10, SEQ ID NO: 11, SEQ ID NO: 12, SEQ ID NO: 13, SEQ ID NO: 15 or SEQ ID NO: 16,
   b) a polynucleotide comprising a polynucleotide sequence at least 90% identical to a polynucleotide sequence of SEQ ID NO: 10, SEQ ID NO: 15 or SEQ ID NO: 16,
   c) a polynucleotide complementary to a polynucleotide of a),
   d) a polynucleotide complementary to a polynucleotide of b) and
   e) an RNA equivalent of a)–d).

6. A method of detecting a target polynucleotide in a sample, said target polynucleotide having a sequence of a polynucleotide of claim 5, the method comprising:
   a) hybridizing the sample with a probe comprising at least 20 contiguous nucleotides comprising a sequence complementary to said target polynucleotide in the sample, and which probe specifically hybridizes to said target polynucleotide, under conditions whereby a hybridization complex is formed between said probe and said target polynucleotide, and
   b) detecting the presence or absence of said hybridization complex, and, optionally, if present, the amount thereof.

7. A method of claim 6, wherein the probe comprises at least 60 contiguous nucleotides.

8. A method of detecting a target polynucleotide in a sample, said target polynucleotide having a sequence of a polynucleotide of claim 5, the method comprising:
   a) amplifying said target polynucleotide using polymerase chain reaction amplification, and
   b) detecting the presence or absence of said amplified target polynucleotide and optionally, if present, the amount thereof.

9. An isolated polynucleotide encoding a polypeptide comprising an amino acid sequence selected from the group consisting of SEQ ID NO: 2, SEQ ID NO: 3, SEQ ID NO: 5, SEQ ID NO: 7 and SEQ ID NO: 8.

10. An isolated polynucleotide of claim 9 comprising a polynucleotide sequence selected from the group consisting of SEQ ID NO: 10, SEQ ID NO: 11, SEQ ID NO: 13, SEQ ID NO: 15 and SEQ ID NO: 16.

11. A method of screening a compound for effectiveness in altering expression of a target polynucleotide, wherein said target polynucleotide comprises a polynucleotide sequence of claim 5, the method comprising:
   a) contacting a sample comprising the target polynucleotide with, under conditions suitable for the expression of the target polynucleotide,
   b) detecting altered expression of the target polynucleotide, and
   c) comparing the expression of the target polynucleotide in the presence of varying amounts of the compound and in the absence of the compound.

* * * * *

SEQUENCE LISTING

<160> NUMBER OF SEQ ID NOS: 16

<210> SEQ ID NO 1
<211> LENGTH: 480
<212> TYPE: PRT
<213> ORGANISM: Homo sapiens
<220> FEATURE:
<221> NAME/KEY: misc_feature
<223> OTHER INFORMATION: Incyte ID No:012033CD1

<400> SEQUENCE: 1

Met Arg Phe Val Val Ala Leu Val Leu Leu Asn Val Ala Ala Ala
 1               5                  10                  15

Gly Ala Val Pro Leu Leu Ala Thr Glu Ser Val Lys Gln Glu Glu
                20                  25                  30

Ala Gly Val Arg Pro Ser Ala Gly Asn Val Ser Thr His Pro Ser
                35                  40                  45

Leu Ser Gln Arg Pro Gly Gly Ser Thr Lys Ser His Pro Glu Pro
                50                  55                  60

Gln Thr Pro Lys Asp Ser Pro Ser Lys Ser Ser Ala Glu Ala Gln
                65                  70                  75

Thr Pro Glu Asp Thr Pro Asn Lys Ser Gly Ala Glu Ala Lys Thr
                80                  85                  90

Gln Lys Asp Ser Ser Asn Lys Ser Gly Ala Glu Ala Lys Thr Gln
                95                  100                 105

Lys Gly Ser Thr Ser Lys Ser Gly Ser Glu Ala Gln Thr Thr Lys
                110                 115                 120

-continued

```
Asp Ser Thr Ser Lys Ser His Ser Glu Leu Gln Thr Pro Lys Asp
            125                 130                 135

Ser Thr Gly Lys Ser Gly Ala Glu Ala Gln Thr Pro Glu Asp Ser
            140                 145                 150

Pro Asn Arg Ser Gly Ala Glu Ala Lys Thr Gln Lys Asp Ser Pro
            155                 160                 165

Ser Lys Ser Gly Ser Glu Ala Gln Thr Thr Lys Asp Val Pro Asn
            170                 175                 180

Lys Ser Gly Ala Asp Gly Gln Thr Pro Lys Asp Gly Ser Ser Lys
            185                 190                 195

Ser Gly Ala Glu Asp Gln Thr Pro Lys Asp Val Pro Asn Lys Ser
            200                 205                 210

Gly Ala Glu Lys Gln Thr Pro Lys Asp Gly Ser Asn Lys Ser Gly
            215                 220                 225

Ala Glu Glu Gln Gly Pro Ile Asp Gly Pro Ser Lys Ser Gly Ala
            230                 235                 240

Glu Glu Gln Thr Ser Lys Asp Ser Pro Asn Lys Val Val Pro Glu
            245                 250                 255

Gln Pro Ser Arg Lys Asp His Ser Lys Pro Ile Ser Asn Pro Ser
            260                 265                 270

Asp Asn Lys Glu Leu Pro Lys Ala Asp Thr Asn Gln Leu Ala Asp
            275                 280                 285

Lys Gly Lys Leu Ser Pro His Ala Phe Lys Thr Glu Ser Gly Glu
            290                 295                 300

Glu Thr Asp Leu Ile Ser Pro Pro Gln Glu Glu Val Lys Ser Ser
            305                 310                 315

Glu Pro Thr Glu Asp Val Glu Pro Lys Glu Ala Glu Asp Asp
            320                 325                 330

Thr Gly Pro Glu Glu Gly Ser Pro Pro Lys Glu Glu Lys Glu Lys
            335                 340                 345

Met Ser Gly Ser Ala Ser Ser Glu Asn Arg Glu Gly Thr Leu Ser
            350                 355                 360

Asp Ser Thr Gly Ser Glu Lys Asp Asp Leu Tyr Pro Asn Gly Ser
            365                 370                 375

Gly Asn Gly Ser Ala Glu Ser Ser His Phe Phe Ala Tyr Leu Val
            380                 385                 390

Thr Ala Ala Ile Leu Val Ala Val Leu Tyr Ile Ala His His Asn
            395                 400                 405

Lys Arg Lys Ile Ile Ala Phe Val Leu Glu Gly Lys Arg Ser Lys
            410                 415                 420

Val Thr Arg Arg Pro Lys Ala Ser Asp Tyr Gln Arg Leu Asp Gln
            425                 430                 435

Lys Tyr Val Leu Ile Leu Asn Val Phe Pro Ala Pro Lys Arg
            440                 445                 450

Ser Phe Leu Pro Gln Val Leu Thr Glu Trp Tyr Ile Pro Leu Glu
            455                 460                 465

Lys Asp Glu Arg His Gln Trp Ile Val Leu Leu Ser Phe Gln Leu
            470                 475                 480
```

<210> SEQ ID NO 2
<211> LENGTH: 140
<212> TYPE: PRT
<213> ORGANISM: Homo sapiens
<220> FEATURE:
<221> NAME/KEY: misc_feature -continued
<223> OTHER INFORMATION: Incyte ID No:1209687CD1

<400> SEQUENCE: 2

Met Ala Ser Val Asp Phe Lys Thr Tyr Val Asp Gln Ala Cys Arg
 1               5                  10                  15

Ala Ala Glu Glu Phe Val Asn Val Tyr Tyr Thr Thr Met Asp Lys
                20                  25                  30

Arg Arg Arg Leu Leu Ser Arg Leu Tyr Met Gly Thr Ala Thr Leu
                35                  40                  45

Val Trp Asn Gly Asn Ala Val Ser Gly Gln Glu Ser Leu Ser Glu
                50                  55                  60

Phe Phe Glu Met Leu Pro Ser Ser Glu Phe Gln Ile Ser Val Val
                65                  70                  75

Asp Cys Gln Pro Val His Asp Glu Ala Thr Pro Ser Gln Thr Thr
                80                  85                  90

Val Leu Val Val Ile Cys Gly Ser Val Lys Phe Glu Gly Asn Lys
                95                  100                 105

Gln Arg Asp Phe Asn Gln Asn Phe Ile Leu Thr Ala Gln Ala Ser
                110                 115                 120

Pro Ser Asn Thr Val Trp Lys Ile Ala Ser Asp Cys Phe Arg Phe
                125                 130                 135

Gln Asp Trp Ala Ser
                140

<210> SEQ ID NO 3
<211> LENGTH: 519
<212> TYPE: PRT
<213> ORGANISM: Homo sapiens
<220> FEATURE:
<221> NAME/KEY: misc_feature
<223> OTHER INFORMATION: Incyte ID No:1717058CD1

<400> SEQUENCE: 3

Met Ala Ala Glu Arg Glu Pro Pro Leu Gly Asp Gly Lys Pro
 1               5                  10                  15

Thr Asp Phe Glu Asp Leu Glu Asp Gly Glu Asp Leu Phe Thr Ser
                20                  25                  30

Thr Val Ser Thr Leu Glu Ser Ser Pro Ser Pro Glu Pro Ala
                35                  40                  45

Ser Leu Pro Ala Glu Asp Ile Ser Ala Asn Ser Asn Gly Pro Lys
                50                  55                  60

Pro Thr Glu Val Val Leu Asp Asp Arg Glu Asp Leu Phe Ala
                65                  70                  75

Glu Ala Thr Glu Glu Val Ser Leu Asp Ser Pro Glu Arg Glu Pro
                80                  85                  90

Ile Leu Ser Ser Glu Pro Ser Pro Ala Val Thr Pro Val Thr Pro
                95                  100                 105

Thr Thr Leu Ile Ala Pro Arg Ile Glu Ser Lys Ser Met Ser Ala
                110                 115                 120

Pro Val Ile Phe Asp Arg Ser Arg Glu Glu Ile Glu Glu Ala
                125                 130                 135

Asn Gly Asp Ile Phe Asp Ile Glu Ile Gly Val Ser Asp Pro Glu
                140                 145                 150

Lys Val Gly Asp Gly Met Asn Ala Tyr Met Ala Tyr Arg Val Thr
                155                 160                 165

Thr Lys Thr Ser Leu Ser Met Phe Ser Lys Ser Glu Phe Ser Val

```
                170                 175                 180
Lys Arg Arg Phe Ser Asp Phe Leu Gly Leu His Ser Lys Leu Ala
            185                 190                 195
Ser Lys Tyr Leu His Val Gly Tyr Ile Val Pro Pro Ala Pro Glu
            200                 205                 210
Lys Ser Ile Val Gly Met Thr Lys Val Lys Val Gly Lys Glu Asp
            215                 220                 225
Ser Ser Ser Thr Glu Phe Val Glu Lys Arg Ala Ala Leu Glu
            230                 235                 240
Arg Tyr Leu Gln Arg Thr Val Lys His Pro Thr Leu Leu Gln Asp
            245                 250                 255
Pro Asp Leu Arg Gln Phe Leu Glu Ser Ser Glu Leu Pro Arg Ala
            260                 265                 270
Val Asn Thr Gln Ala Leu Ser Gly Ala Gly Ile Leu Arg Met Val
            275                 280                 285
Asn Lys Ala Ala Asp Ala Val Asn Lys Met Thr Ile Lys Met Asn
            290                 295                 300
Glu Ser Asp Ala Trp Phe Glu Glu Lys Gln Gln Gln Phe Glu Asn
            305                 310                 315
Leu Asp Gln Gln Leu Arg Lys Leu His Val Ser Val Glu Ala Leu
            320                 325                 330
Val Cys His Arg Lys Glu Leu Ser Ala Asn Thr Ala Ala Phe Ala
            335                 340                 345
Lys Ser Ala Ala Met Leu Gly Asn Ser Glu Asp His Thr Ala Leu
            350                 355                 360
Ser Arg Ala Leu Ser Gln Leu Ala Glu Val Glu Glu Lys Ile Asp
            365                 370                 375
Gln Leu His Gln Glu Gln Ala Phe Ala Asp Phe Tyr Met Phe Ser
            380                 385                 390
Glu Leu Leu Ser Asp Tyr Ile Arg Leu Ile Ala Ala Val Lys Gly
            395                 400                 405
Val Phe Asp His Arg Met Lys Cys Trp Gln Lys Trp Glu Asp Ala
            410                 415                 420
Gln Ile Thr Leu Leu Lys Lys Arg Glu Ala Glu Ala Lys Met Met
            425                 430                 435
Val Ala Asn Lys Pro Asp Lys Ile Gln Gln Ala Lys Asn Glu Ile
            440                 445                 450
Arg Glu Trp Glu Ala Lys Val Gln Gln Gly Arg Asp Phe Glu
            455                 460                 465
Gln Ile Ser Lys Thr Ile Arg Lys Glu Val Gly Arg Phe Glu Lys
            470                 475                 480
Glu Arg Val Lys Asp Phe Lys Thr Val Ile Ile Lys Tyr Leu Glu
            485                 490                 495
Ser Leu Val Gln Thr Gln Gln Gln Leu Ile Lys Tyr Trp Glu Ala
            500                 505                 510
Phe Leu Pro Glu Ala Lys Ala Ile Ala
            515

<210> SEQ ID NO 4
<211> LENGTH: 613
<212> TYPE: PRT
<213> ORGANISM: Homo sapiens
<220> FEATURE:
<221> NAME/KEY: misc_feature
<223> OTHER INFORMATION: Incyte ID No:1749964CD1
```

-continued

<400> SEQUENCE: 4

```
Met Ala Ala Thr Ala Val Ala Ala Val Ala Gly Thr Glu Ser
 1               5                  10                  15

Ala Gln Gly Pro Pro Gly Pro Ala Ala Ser Leu Glu Leu Trp Leu
                 20                  25                  30

Asn Lys Ala Thr Asp Pro Ser Met Ser Glu Gln Asp Trp Ser Ala
                 35                  40                  45

Ile Gln Asn Phe Cys Glu Gln Val Asn Thr Asp Pro Asn Gly Pro
                 50                  55                  60

Thr His Ala Pro Trp Leu Leu Ala His Lys Ile Gln Ser Pro Gln
                 65                  70                  75

Glu Lys Glu Ala Leu Tyr Ala Leu Thr Val Leu Glu Met Cys Met
                 80                  85                  90

Asn His Cys Gly Glu Lys Phe His Ser Glu Val Ala Lys Phe Arg
                 95                 100                 105

Phe Leu Asn Glu Leu Ile Lys Val Leu Ser Pro Lys Tyr Leu Gly
                110                 115                 120

Ser Trp Ala Thr Gly Lys Val Lys Gly Arg Val Ile Glu Ile Leu
                125                 130                 135

Phe Ser Trp Thr Val Trp Phe Pro Glu Asp Ile Lys Ile Arg Asp
                140                 145                 150

Ala Tyr Gln Met Leu Lys Lys Gln Gly Ile Ile Lys Gln Asp Pro
                155                 160                 165

Lys Leu Pro Val Asp Lys Ile Leu Pro Pro Ser Pro Trp Pro
                170                 175                 180

Lys Ser Ser Ile Phe Asp Ala Asp Glu Glu Lys Ser Lys Leu Leu
                185                 190                 195

Thr Arg Leu Leu Lys Ser Asn His Pro Glu Asp Leu Gln Ala Ala
                200                 205                 210

Asn Arg Leu Ile Lys Asn Leu Val Lys Glu Gln Glu Lys Ser
                215                 220                 225

Glu Lys Val Ser Lys Arg Val Ser Ala Val Glu Glu Val Arg Ser
                230                 235                 240

His Val Lys Val Leu Gln Glu Met Leu Ser Met Tyr Arg Arg Pro
                245                 250                 255

Gly Gln Ala Pro Pro Asp Gln Glu Ala Leu Gln Val Val Tyr Glu
                260                 265                 270

Arg Cys Glu Lys Leu Arg Pro Thr Leu Phe Arg Leu Ala Ser Asp
                275                 280                 285

Thr Thr Asp Asp Asp Ala Leu Ala Glu Ile Leu Gln Ala Asn
                290                 295                 300

Asp Leu Leu Thr Gln Gly Val Leu Leu Tyr Lys Gln Val Met Glu
                305                 310                 315

Gly Arg Val Thr Phe Gly Asn Arg Val Thr Ser Ser Leu Gly Asp
                320                 325                 330

Ile Pro Val Ser Arg Val Phe Gln Asn Pro Ala Gly Cys Met Lys
                335                 340                 345

Thr Cys Pro Leu Ile Asp Leu Glu Val Asp Asn Gly Pro Ala Gln
                350                 355                 360

Met Gly Thr Val Val Pro Ser Leu Leu His Gln Asp Leu Ala Ala
                365                 370                 375

Leu Gly Ile Ser Asp Ala Pro Val Thr Gly Met Val Ser Gly Gln
```

-continued

```
                    380                 385                 390
Asn Cys Cys Glu Glu Lys Arg Asn Pro Ser Ser Thr Leu Pro
                395                 400                 405
Gly Gly Gly Val Gln Asn Pro Ser Ala Asp Arg Asn Leu Leu Asp
            410                 415                 420
Leu Leu Ser Ala Gln Pro Ala Pro Cys Pro Leu Asn Tyr Val Ser
            425                 430                 435
Gln Lys Ser Val Pro Lys Glu Val Pro Pro Gly Thr Lys Ser Ser
            440                 445                 450
Pro Gly Trp Ser Trp Glu Ala Gly Pro Leu Ala Pro Ser Pro Ser
            455                 460                 465
Ser Gln Asn Thr Pro Leu Ala Gln Val Phe Val Pro Leu Glu Ser
            470                 475                 480
Val Lys Pro Ser Ser Leu Pro Pro Leu Ile Val Tyr Asp Arg Asn
            485                 490                 495
Gly Phe Arg Ile Leu Leu His Phe Ser Gln Thr Gly Ala Pro Gly
            500                 505                 510
His Pro Glu Val Gln Val Leu Leu Thr Met Met Ser Thr Ala
            515                 520                 525
Pro Gln Pro Val Trp Asp Ile Met Phe Gln Val Ala Val Pro Lys
            530                 535                 540
Ser Met Arg Val Lys Leu Gln Pro Ala Ser Ser Ser Lys Leu Pro
            545                 550                 555
Ala Phe Ser Pro Leu Met Pro Pro Ala Val Ile Ser Gln Met Leu
            560                 565                 570
Leu Leu Asp Asn Pro His Lys Glu Pro Ile Arg Leu Arg Tyr Lys
            575                 580                 585
Leu Thr Phe Asn Gln Gly Gly Gln Pro Phe Ser Glu Val Gly Glu
            590                 595                 600
Val Lys Asp Phe Pro Asp Leu Ala Val Leu Gly Ala Ala
            605                 610
```

<210> SEQ ID NO 5
<211> LENGTH: 719
<212> TYPE: PRT
<213> ORGANISM: Homo sapiens
<220> FEATURE:
<221> NAME/KEY: misc_feature
<223> OTHER INFORMATION: Incyte ID No:1856357CD1

<400> SEQUENCE: 5

```
Met Ser Val Asp Lys Ala Glu Leu Cys Gly Ser Leu Leu Thr Trp
  1               5                  10                  15
Leu Gln Thr Phe His Val Pro Ser Pro Cys Ala Ser Pro Gln Asp
                 20                  25                  30
Leu Ser Ser Gly Leu Ala Val Ala Tyr Val Leu Asn Gln Ile Asp
                 35                  40                  45
Pro Ser Trp Phe Asn Glu Ala Trp Leu Gln Gly Ile Ser Glu Asp
                 50                  55                  60
Pro Gly Pro Asn Trp Lys Leu Lys Val Ser Asn Leu Lys Met Val
                 65                  70                  75
Leu Arg Ser Leu Val Glu Tyr Ser Gln Asp Val Leu Ala His Pro
                 80                  85                  90
Val Ser Glu Glu His Leu Pro Asp Val Ser Leu Ile Gly Glu Phe
                 95                  100                 105
```

-continued

Ser Asp Pro Ala Glu Leu Gly Lys Leu Leu Gln Leu Val Leu Gly
            110                 115                 120

Cys Ala Ile Ser Cys Glu Lys Lys Gln Asp His Ile Gln Arg Ile
            125                 130                 135

Met Thr Leu Glu Glu Ser Val Gln His Val Val Met Glu Ala Ile
            140                 145                 150

Gln Glu Leu Met Thr Lys Asp Thr Pro Asp Ser Leu Ser Pro Glu
            155                 160                 165

Thr Tyr Gly Asn Phe Asp Ser Gln Ser Arg Arg Tyr Tyr Phe Leu
            170                 175                 180

Ser Glu Glu Ala Glu Glu Gly Asp Glu Leu Gln Gln Arg Cys Leu
            185                 190                 195

Asp Leu Glu Arg Gln Leu Met Leu Leu Ser Glu Glu Lys Gln Ser
            200                 205                 210

Leu Ala Gln Glu Asn Ala Gly Leu Arg Glu Arg Met Gly Arg Pro
            215                 220                 225

Glu Gly Glu Gly Thr Pro Gly Leu Thr Ala Lys Lys Leu Leu Leu
            230                 235                 240

Leu Gln Ser Gln Leu Glu Gln Leu Gln Glu Asn Phe Arg Leu
            245                 250                 255

Glu Ser Gly Arg Glu Asp Glu Arg Leu Arg Cys Ala Glu Leu Glu
            260                 265                 270

Arg Glu Val Ala Glu Leu Gln His Arg Asn Gln Ala Leu Thr Ser
            275                 280                 285

Leu Ala Gln Glu Ala Gln Ala Leu Lys Asp Glu Met Asp Glu Leu
            290                 295                 300

Arg Gln Ser Ser Glu Arg Ala Gly Gln Leu Glu Ala Thr Leu Thr
            305                 310                 315

Ser Cys Arg Arg Arg Leu Gly Glu Leu Arg Glu Leu Arg Arg Gln
            320                 325                 330

Val Arg Gln Leu Glu Glu Arg Asn Ala Gly His Ala Glu Arg Thr
            335                 340                 345

Arg Gln Leu Glu Asp Glu Leu Arg Arg Ala Gly Ser Leu Arg Ala
            350                 355                 360

Gln Leu Glu Ala Gln Arg Arg Gln Val Gln Glu Leu Gln Gly Gln
            365                 370                 375

Arg Gln Glu Glu Ala Met Lys Ala Glu Lys Trp Leu Phe Glu Cys
            380                 385                 390

Arg Asn Leu Glu Glu Lys Tyr Glu Ser Val Thr Lys Glu Lys Glu
            395                 400                 405

Arg Leu Leu Ala Glu Arg Asp Ser Leu Arg Glu Ala Asn Glu Glu
            410                 415                 420

Leu Arg Cys Ala Gln Leu Gln Pro Arg Gly Leu Thr Gln Ala Asp
            425                 430                 435

Pro Ser Leu Asp Pro Thr Ser Thr Pro Val Asp Asn Leu Ala Ala
            440                 445                 450

Glu Ile Leu Pro Ala Glu Leu Arg Glu Thr Leu Leu Arg Leu Gln
            455                 460                 465

Leu Glu Asn Lys Arg Leu Cys Arg Gln Glu Ala Ala Asp Arg Glu
            470                 475                 480

Arg Gln Glu Glu Leu Gln Arg His Leu Glu Asp Ala Asn Arg Ala
            485                 490                 495

Arg His Gly Leu Glu Thr Gln His Arg Leu Asn Gln Gln Gln Leu

-continued

```
                    500                 505                 510

Ser Glu Leu Arg Ala Gln Val Glu Asp Leu Gln Lys Ala Leu Gln
            515                 520                 525

Glu Gln Gly Gly Lys Thr Glu Asp Ala Ile Ser Ile Leu Leu Lys
        530                 535                 540

Arg Lys Leu Glu Glu His Leu Gln Lys Leu His Glu Ala Asp Leu
    545                 550                 555

Glu Leu Gln Arg Lys Arg Glu Tyr Ile Glu Glu Leu Glu Pro Pro
        560                 565                 570

Thr Asp Ser Ser Thr Ala Arg Arg Ile Glu Glu Leu Gln His Asn
    575                 580                 585

Leu Gln Lys Lys Asp Ala Asp Leu Arg Ala Met Glu Glu Arg Tyr
        590                 595                 600

Arg Arg Tyr Val Asp Lys Ala Arg Met Val Met Gln Thr Met Glu
    605                 610                 615

Pro Lys Gln Arg Pro Ala Ala Gly Ala Pro Pro Glu Leu His Ser
        620                 625                 630

Leu Arg Thr Gln Leu Arg Glu Arg Asp Val Arg Ile Arg His Leu
    635                 640                 645

Glu Met Asp Phe Glu Lys Ser Arg Ser Gln Arg Glu Gln Glu Glu
        650                 655                 660

Lys Leu Leu Ile Ser Ala Trp Tyr Asn Met Gly Met Ala Leu Gln
    665                 670                 675

Gln Arg Ala Gly Glu Glu Arg Ala Pro Ala His Ala Gln Ser Phe
        680                 685                 690

Leu Ala Gln Gln Arg Leu Ala Thr Asn Ser Arg Arg Gly Pro Leu
    695                 700                 705

Gly Arg Leu Ala Ser Leu Asn Leu Arg Pro Thr Asp Lys His
        710                 715

<210> SEQ ID NO 6
<211> LENGTH: 175
<212> TYPE: PRT
<213> ORGANISM: Homo sapiens
<220> FEATURE:
<221> NAME/KEY: misc_feature
<223> OTHER INFORMATION: Incyte ID No:1871275CD1

<400> SEQUENCE: 6

Met Gly Ile Leu Leu Gly Leu Leu Leu Gly His Leu Thr Val
  1               5                  10                  15

Asp Thr Tyr Gly Arg Pro Ile Leu Glu Val Pro Glu Ser Val Thr
            20                  25                  30

Gly Pro Trp Lys Gly Asp Val Asn Leu Pro Cys Thr Tyr Asp Pro
        35                  40                  45

Leu Gln Gly Tyr Thr Gln Val Leu Val Lys Trp Leu Val Gln Arg
    50                  55                  60

Gly Ser Asp Pro Val Thr Ile Phe Leu Arg Asp Ser Ser Gly Asp
        65                  70                  75

His Ile Gln Gln Ala Lys Tyr Gln Gly Arg Leu His Val Ser His
    80                  85                  90

Lys Val Pro Gly Asp Val Ser Leu Gln Leu Ser Thr Leu Glu Met
        95                  100                 105

Asp Asp Arg Ser His Tyr Thr Cys Glu Val Thr Trp Gln Thr Pro
    110                 115                 120
```

-continued

Asp Gly Asn Gln Val Val Arg Asp Lys Ile Thr Glu Leu Arg Val
            125                 130                 135

Gln Lys His Ser Ser Lys Leu Leu Lys Thr Lys Thr Glu Ala Pro
            140                 145                 150

Thr Thr Met Thr Tyr Pro Leu Lys Ala Thr Ser Thr Val Lys Gln
            155                 160                 165

Ser Trp Asp Trp Thr Thr Asp Met Asp Gly
            170                 175

<210> SEQ ID NO 7
<211> LENGTH: 142
<212> TYPE: PRT
<213> ORGANISM: Homo sapiens
<220> FEATURE:
<221> NAME/KEY: misc_feature
<223> OTHER INFORMATION: Incyte ID No:2645806CD1

<400> SEQUENCE: 7

Met Ala Thr Ser Leu Asp Phe Lys Thr Tyr Val Asp Gln Ala Cys
  1               5                  10                  15

Arg Ala Ala Glu Glu Phe Val Asn Ile Tyr Tyr Glu Thr Met Asp
             20                  25                  30

Lys Arg Arg Arg Ala Leu Thr Arg Leu Tyr Leu Asp Lys Ala Thr
             35                  40                  45

Leu Ile Trp Asn Gly Asn Ala Val Ser Gly Leu Asp Ala Leu Asn
             50                  55                  60

Asn Phe Phe Asp Thr Leu Pro Ser Ser Glu Phe Gln Val Asn Met
             65                  70                  75

Leu Asp Cys Gln Pro Val His Glu Gln Ala Thr Gln Ser Gln Thr
             80                  85                  90

Thr Val Leu Val Val Thr Ser Gly Thr Val Lys Phe Asp Gly Asn
             95                 100                 105

Lys Gln His Phe Phe Asn Gln Asn Phe Leu Leu Thr Ala Gln Ser
            110                 115                 120

Thr Pro Asn Asn Thr Val Trp Lys Ile Ala Ser Asp Cys Phe Arg
            125                 130                 135

Phe Gln Asp Trp Ser Ser Ser
            140

<210> SEQ ID NO 8
<211> LENGTH: 248
<212> TYPE: PRT
<213> ORGANISM: Homo sapiens
<220> FEATURE:
<221> NAME/KEY: misc_feature
<223> OTHER INFORMATION: Incyte ID No:3437773CD1

<400> SEQUENCE: 8

Met Ser Val Ser Leu Pro Leu Thr Val Met Val Arg Glu Arg Asp
  1               5                  10                  15

Trp Ile Gly Ile His Leu Phe Ser Leu Tyr Leu Ser Leu Pro Val
             20                  25                  30

Gly Ile Pro Asp Phe Gly Ser Ile Trp Ser Asp Phe Leu Phe Lys
             35                  40                  45

Phe Leu Val Ile Gly Ser Ala Gly Thr Gly Lys Ser Cys Leu Leu
             50                  55                  60

His Gln Phe Ile Glu Asn Lys Phe Lys Gln Asp Ser Asn His Thr
             65                  70                  75

```
Ile Gly Val Glu Phe Gly Ser Arg Val Asn Val Gly Lys
             80                  85                  90

Thr Val Lys Leu Gln Ile Trp Asp Thr Ala Gly Gln Glu Arg Phe
         95                 100                 105

Arg Ser Val Thr Arg Ser Tyr Tyr Arg Gly Ala Ala Gly Ala Leu
            110                 115                 120

Leu Val Tyr Asp Ile Thr Ser Arg Glu Thr Tyr Asn Ser Leu Ala
            125                 130                 135

Ala Trp Leu Thr Asp Ala Arg Thr Leu Ala Ser Pro Asn Ile Val
            140                 145                 150

Val Ile Leu Cys Gly Asn Lys Lys Asp Leu Asp Pro Glu Arg Glu
            155                 160                 165

Val Thr Phe Leu Glu Ala Ser Arg Phe Ala Gln Glu Asn Glu Leu
            170                 175                 180

Met Phe Leu Glu Thr Ser Ala Leu Thr Gly Glu Asn Val Glu Glu
            185                 190                 195

Ala Phe Leu Lys Cys Ala Arg Thr Ile Leu Asn Lys Ile Asp Ser
            200                 205                 210

Gly Glu Leu Asp Pro Glu Arg Met Gly Ser Gly Ile Gln Tyr Gly
            215                 220                 225

Asp Ala Ser Leu Arg Gln Leu Arg Gln Pro Arg Ser Ala Gln Ala
            230                 235                 240

Val Ala Pro Gln Pro Cys Gly Cys
            245

<210> SEQ ID NO 9
<211> LENGTH: 1630
<212> TYPE: DNA
<213> ORGANISM: Homo sapiens
<220> FEATURE:
<221> NAME/KEY: misc_feature
<223> OTHER INFORMATION: Incyte ID No:012033CB1

<400> SEQUENCE: 9
cgctatccga gcaggatgcg gttcgtggtt gccttggtcc tcctgaacgt cgcagcggcg      60
ggagccgtgc cgctcttggc caccgaaagc gtcaagcaag aagaagctgg agtacggcct     120
tctgcaggaa acgtctccac ccaccccagc ttgagccaac ggcctggagg ctctaccaag     180
tcgcatccgg agccgcagac tccaaaagac agccctagca gtcgagtgc ggaggcgcag      240
accccagaag acaccccaa caagtcgggt gcggaggcaa agacccaaaa agacagctcc      300
aacaagtcgg gtgcggaggc aaagacccaa aaaggcagca ctagcaagtc gggttcggag     360
gcgcagacca caaagacag cactagtaag tcgcattcgg agctgcagac tccaaaagac      420
agcactggca atcgggtgc ggaggcgcag accccagaag acagcccaa caggtcgggt       480
gcggaggcaa agacccaaaa agacagccct agcaagtcag gttcggaggc gcagaccaca     540
aaagatgtcc ctaataagtc gggtgcggac ggccagaccc aaaagacgg ctccagcaag      600
tcgggtgcgg aggatcagac cccaaaagac gtccctaaca gtcgggtgc ggagaagcag      660
actccaaaag acggctctaa caagtccggt gcagaggagc agggcccaat agacgggccc     720
agcaagtcgg gtgcggagga gcagacctca aaagacagcc taacaaggt ggttccagag      780
cagccttccc ggaaagacca ttccaagccc atctccaacc cttctgataa caaggagctc     840
cccaaggctg acacaaacca gcttgctgac aaagggaagc tttctcctca tgctttcaaa     900
accgaatctg gggaggaaac tgacctcatt tctcccccgc aggaggaagt taagtcttca     960
```

-continued

| | |
|---|---|
| gagcctactg aggatgtgga gcccaaagag gctgaagatg atgatacagg acccgaggag | 1020 |
| ggctcaccgc ccaaagaaga gaaagaaaag atgtccggtt ctgcctccag tgagaaccgt | 1080 |
| gaagggacac tttcggattc cacgggtagc gagaaggatg acctttatcc gaacggttct | 1140 |
| ggaaatggca gcgcggagag cagccacttc tttgcatatc tggtgactgc agccattctt | 1200 |
| gtggctgtcc tctatatcgc tcatcacaac aagcggaaga tcattgcttt tgtcctggaa | 1260 |
| ggaaaaagat ctaaagtcac ccggcggcca aaggccagtg actaccaacg tttggaccag | 1320 |
| aagtatgtct taattctgaa tgttttccct gcacctccta aaagatcttt tctcccccaa | 1380 |
| gtcctaacag aatggtatat tcctctggaa aaagatgaac gtcaccaatg gattgtgctg | 1440 |
| ctctcgtttc agctttgatt tttttgtcct tgagaacctt gtcctccctg ctgatttgtt | 1500 |
| tctaaatcaa aagaaatgaa gaaaaaagta ctgtgacctg agagacaccc tcctctagaa | 1560 |
| tttagtggcg ggtctgggct ggcagaggta gggggctgct ttgggctttg cacctgcact | 1620 |
| ttggtgacat | 1630 |

<210> SEQ ID NO 10
<211> LENGTH: 830
<212> TYPE: DNA
<213> ORGANISM: Homo sapiens
<220> FEATURE:
<221> NAME/KEY: misc_feature
<223> OTHER INFORMATION: Incyte ID No:1209687CB1

<400> SEQUENCE: 10

| | |
|---|---|
| tgaactttgg cattcacgtg gcttctcttc aaccttactt ccctgcagcc cctggttccc | 60 |
| caaggcagag gaaataccct ggtggagccc tccttccata gaaccagaga tggcatctgt | 120 |
| ggatttcaag acctatgtgg atcaggcctg cagagctgct gaggagtttg tcaatgtcta | 180 |
| ctacaccacc atggataagc ggcggcgttt gctgtcccgc ctgtacatgg gcacagccac | 240 |
| cctggtctgg aatggcaatg ctgtttcagg acaagaatcc ttgagtgagt tttttgaaat | 300 |
| gttgccttcc agcgagttcc aaatcagcgt ggtagactgc cagcctgttc atgatgaagc | 360 |
| cacaccaagc cagaccacgg tccttgttgt catctgtgga tcagtgaagt ttgaggggaa | 420 |
| caaacaacgg gacttcaacc agaacttcat cctgaccgcc caggcctcac ccagcaacac | 480 |
| agtgtggaag atcgcaagtg actgcttccg cttccaggac tgggccagct agtgggggtg | 540 |
| gcagaggtct ctttgcttca ttcagcccta gctctgtaga gaaatgcaaa cctcgactct | 600 |
| caaggatgtg aggaacacaa gttcatttct gttgttgcgg agacactgca gactccactg | 660 |
| tgccgaggtt gaactctttt tgttgctca agttctagga gtccctttcc tgaatatata | 720 |
| cttgttttgtc atagtttcct tttcaaagta gtaaactttt ctattttt c acttgcccag | 780 |
| tagagactct gattctggaa attctgacaa ataatttaat aatacacatg | 830 |

<210> SEQ ID NO 11
<211> LENGTH: 2025
<212> TYPE: DNA
<213> ORGANISM: Homo sapiens
<220> FEATURE:
<221> NAME/KEY: misc_feature
<223> OTHER INFORMATION: Incyte ID No:1717058CB1

<400> SEQUENCE: 11

| | |
|---|---|
| gtgagcgaag atggcggccg agagggaacc tcctccgctg ggggacggga agcccaccga | 60 |
| ctttgaggat ctggaggacg gagaggacct gttcaccagc actgtctcca ccctagagtc | 120 |
| aagtccatca tctccagaac cagctagtct tcctgcagaa gatattagtg caaactccaa | 180 |

-continued

```
tggcccaaaa cccacagaag ttgtattaga tgatgacaga gaagatcttt ttgcagaagc      240
cacagaagaa gtttctttgg acagccctga aagggaacct atcctatcct cggaaccttc      300
tcctgcagtc acacctgtca ctcctactac actcattgct cctagaattg aatcaaagag      360
tatgtctgct cccgtgatct tgatagatc cagggaagag attgaagaag aagcaaatgg       420 agacatttt gacatagaaa ttggtgtatc agatccagaa aaagttggtg atggcatgaa       480
tgcctatatg gcatatagag taacaacaaa gacatctctt tccatgttca gtaagagtga      540
attttcagtg aaaagaagat tcagcgactt tcttggtttg cacagcaaat tagcaagcaa      600
atatttacat gttggttata ttgtgccacc agctccagaa aagagtatag tagggatgac      660
caaggtcaaa gtgggtaaag aagactcatc atccactgag tttgtagaaa acggagagc       720 agctcttgaa aggtatcttc aaagaacagt aaaacatcca actttactac aggatcctga      780
tttaaggcag ttcttggaaa gttcagagct gcctagagca gttaatacac aggctctgag      840
tggagcagga atattgagga tggtgaacaa ggctgccgac gctgtcaaca aaatgacaat      900
caagatgaat gaatcggatg catggtttga agaaaagcag cagcaatttg agaatctgga      960
tcagcaactt aggaaacttc atgtcagtgt tgaagccttg gtctgtcata gaaaagaact      1020
ttcagccaac acagctgcct ttgctaaaag tgctgccatg ttaggtaatt ctgaggatca     1080
tactgcttta tctagagctt tgtctcagct tgcagaggtt gaggagaaga tagaccagtt     1140
acatcaagaa caagcttttg ctgactttta tatgttttca gaactactta gtgactacat     1200
tcgtcttatt gctgcagtga aagtgtgtt tgaccatcga atgaagtgct ggcagaaatg      1260
ggaagatgct caaattactt tgctcaaaaa acgtgaagct gaagcaaaaa tgatggttgc     1320
taacaaacca gataaaatac agcaagctaa aaatgaaata agagagtggg aggcgaaagt     1380
gcaacagggg gaaagagatt ttgaacagat atctaaaacg attcgaaaag aagtgggaag     1440
atttgagaaa gaacgagtga aggatttta aaccgttatc atcaagtact tagaatcact      1500
agttcaaaca caacaacagc tgataaaata ctgggaagca ttcctacctg aagccaaagc     1560
cattgcctag caataagatt gttgccgtta agaagaacctt ggatgttgtt ccagttatgc    1620
tggattccac agtgaaatca tttaaaacca tctaaataaa ccactatata ttttatgaat    1680
tacatgtggt tttatataca cacacacaca cacacacaca ctctgacatt ttattacaag    1740
ctgcatgtcc tgaccctctt tgaattaagt ggactgtggc atgacattct gcaatacttt    1800
gctgaattga acactattgt gtcttaaata cttgcactaa atagtgcact gcaagaccag    1860
aaaattttac aatatttttt ctttacaata tgttctgtag tatgtttacc ctctttatga    1920
agtgaattac caatgctttg aataatgttc acttatacat tcctgtacag aaattacgat    1980
tttgtgatta cagtaataaa atgatattcc ttgtgaaaaa aaaaa                    2025
```

```
<210> SEQ ID NO 12
<211> LENGTH: 3465
<212> TYPE: DNA
<213> ORGANISM: Homo sapiens
<220> FEATURE:
<221> NAME/KEY: misc_feature
<223> OTHER INFORMATION: Incyte ID No:1749964CB1

<400> SEQUENCE: 12
```

```
acggccagtg caagctaaaa ttaaccctca ctaaagggaa taagcttgcg ccgcggcgtc       60
ggggctggag cgatggcggc gaccgcggtg gcggcggctg tggcgggaac cgagtcggcc      120
cagggtcccc cggggcccggc agcgtcgctg gagctgtggc tgaacaaagc cacagaccca     180
```

```
agcatgtcgg aacaggattg gtcagctatc cagaatttct gtgagcaggt gaacactgac    240
cccaatggcc ccacacatgc gccctggcta ctggcccaca agatccagtc tccgcaagag    300
aaggaagctc tttatgcctt aacggtgctg agatgtgca tgaaccactg tggggagaag    360
ttccacagcg aggtggccaa atttcgtttc ctgaacgaac tgatcaaagt gttgtcccca    420
aagtacctgg ggtcctgggc cacaggaaaa gttaaggaa gagtcattga aatactcttc     480
agttggacag tctggtttcc ggaagacatc aagattcgag acgcttatca gatgctgaag    540
aaacaaggaa ttataaaaca agaccctaaa ctaccagtgg ataaaatctt accccccacca   600 tctccctggc ccaagagctc catctttgat gctgatgaag aaaagtccaa gcttctgaca    660
aggcttctaa agagcaacca ccccgaggac cttcaggctg caaaccggtt aatcaagaat    720
ttggtcaagg aggaacaaga aaaatcggag aaggtgtcca agagggtcag tgcggtggag    780
gaagtgcgaa gccatgtgaa ggtgctgcag gagatgctga gcatgtaccg caggccaggg    840
caggccccgc ccgaccagga ggccctgcag gtcgtgtatg agaggtgtga aaagctgcgg    900
cccacgctgt tccggttggc gagtgacacc actgatgacg atgatgcact cgcgaaatt     960 ctccaggcaa atgacctcct cacccaagga gttctgctgt acaaacaggt gatggagggc    1020
cgggtcacct ttggaaacag agtgaccagc tcattgggag acatccctgt ctccagagtc    1080
tttcagaatc cagcaggctg catgaagacc tgccccctga ttgacttgga ggtggacaat    1140
ggacctgcgc agatggggac tgtggtgcca tctttgcttc atcaggacct ggcagccttg    1200
ggaatcagtg atgctcctgt tacaggcatg gtttctggtc agaattgctg tgaggaaaag    1260
aggaatccct cctccagcac gctgccaggc ggtggtgttc agaacccttc tgcagacagg    1320
aatttgctgg acctcctctc agcacagcca gctccgtgcc ctctgaatta tgtttcgcag    1380
aaaagtgtcc ccaaggaagt gccaccaggt actaagtcct ctccaggttg gtcctgggag    1440
gctggcccgt tggctccttc cccatcttca cagaatacac ctctggctca agtgtttgtc    1500
cctttggagt ctgttaagcc cagcagcctg ccgcctctca ttgtgtatga ccggaatgga    1560
ttcagaattc tgctccactt ctcccagacg ggagcccctg gcacccaga ggtacaggtg      1620 ctgctcttga ccatgatgag cacggctccc cagcctgtct gggatatcat gtttcaagtg    1680
gctgtgccaa agtcaatgag agtgaagctg cagccggcat ccagctccaa gcttcctgca    1740
ttcagtcctt tgatgcctcc agctgtgata tctcagatgc tgctgcttga caatccacac    1800
aaagaaccta tccgcttacg gtacaagctg acattcaacc aaggtggaca gcctttcagc    1860
gaagtaggag aagtgaaaga cttcccagac ctggctgtct gggcgcagc ctaacttttc      1920 acaagatgga cccttcattt caagcttagg ctggcgttac ttttgctgtc tagtcaggac    1980
taatcacggt gtttcagtgc ggagtgccaa gagtcctatc ctgacgtcag gctctgggtg    2040
tcaacctctg acttattctg cagatgctct gtgtgtgtgt gtgtgtgtgt gtgtgtgtgt    2100
gtgtgtgtgt gtgtgtgtgt gtgttcgggg agagggtggt agcacagggc ttgggatatc    2160
ggcagtgtgg gaaatgcgaa gtatttctca tcatcatcat ctctgctaca gtcatgtttc    2220
tgcatgtcag cgagcgacac tgtccctgcc tcaggttgga ggttttatca gccaaagtgt    2280 tttttttcatg tatcgttcgt tccattcatc cactctgtgc cttgtcagcc tttgaaaggc   2340
ttggttgctc ccaggctgct gttctcaggg accttaaaag ggacctggtt agtcttgggg    2400
cagagagtat ctacttgggc actctcttcc aagaaagacc ttgtctccat tttcattaga    2460
caatgcttct tgtgtgtgtt ctggaagatc ttctaaatgg aatgcttgtt gcactgttcc    2520
```

-continued

```
caggcgagtg gctgccatga gacctgagga ccacacttgg gggaccaatc atgtccttca    2580
ccactgtgcc ttagaatcgc ccctggacag agttcctggg cagaggggaa agcagctccc    2640
aggccttact caggcctcag gtccatgggt tgggcagcca gtctgggccc ttctcaggat    2700
cctcatctcc atcctcatcc tcttccttca cagcatttac ttggagctct tgtgacaca    2760 ccatgtcagt catgatgaat cggccaacag ccagcccttg ccagctgacg tcacagtcta    2820
agatgggaaa ctgtggtaca gatagacatg aagagagctt agcagtgatt gaggtggtga    2880
ctaaatatac agtcattgaa taaataccat gtagcaagtg tactttgtgg agtgttgagt    2940
aagtggaaaa tggaaagcca gttgcattta gagatgatag gcctaaaggg aactgtcttc    3000
tgtcgagaag taaaggaaac ttcatgaagg atgtagaagc ttagctgcct cagagaagag    3060
agaacctgaa gatctgaggc aagctggaca ggagaggtgg atatttgttg atggaagaat    3120
tcaagtttat aatcaattcc cacttagcac ctactgtgtg ctaggaactt gaatgtgtat    3180
gtttgacaag tcctgcttgg cctgatgggt gggagaagga acctgagcct ggctgagatg    3240
gctaggcgga gggctttgaa gtccaagcag ctgaactggc tgggtgggtt tctacctttg    3300
aaactgcaag acttgtttgg agctcttaat tacaatatct gatattttta cagtctgatc    3360
ttttgacttc tacatatagt ggaaatctgc caatactaat tggtggagat gggaactgta    3420
aaagatcaag tatgctaatt ttaagcaaat gtaaaaactc aataa                   3465
```

<210> SEQ ID NO 13
<211> LENGTH: 2528
<212> TYPE: DNA
<213> ORGANISM: Homo sapiens
<220> FEATURE:
<221> NAME/KEY: misc_feature
<223> OTHER INFORMATION: Incyte ID No:1856357CB1

<400> SEQUENCE: 13

```
gctcgctggt ggcggacccg gaggctgctg cggcgccggg gctccgtggc ctggattgaa      60
tccgatcggg agccatgagc gtggacaaag ctgagctatg cgggtctctg ctcacctggt     120
tacagacgtt ccacgttccg tctccctgtg ccagccctca ggacctgagc agcggccttg     180
ccgtagccta tgtgctgaac cagatagacc cctcctggtt caacgaggca tggctccagg     240
gcatctcgga agatccaggt cccaactgga agctgaaggt cagcaatctg aagatggtct     300
tacggagcct agtagagtac tcccaggatg tcctggcgca tcctgtgtca gaagagcatc     360
tcccagatgt gagcctcatt ggagagttct cagacccggc agagctcggc aagctgcttc     420
agctggtgct gggctgtgcc atcagttgcg agaaaaagca ggaccacatc cagagaatca     480
tgacgctgga agaatcggtt cagcatgtgg tgatggaagc catccaagag ctcatgacca     540
aagacactcc tgactccctg tcaccagaga cgtatggcaa ctttgacagc cagtcccgca     600
ggtactattt cctaagtgag gaggctgagg aggggggacga attacagcag cgctgtctgg     660
atctggagcg gcagctgatg ctcctgtcag aggagaagca gagcctggcg caagagaatg     720
cagggctgcg ggagcggatg ggccggcctg aaggcgaggg taccccaggt ctcactgcca     780
agaagctgct gctgctgcaa tcccagctgg agcagttgca ggaggagaac ttcaggctgg     840
agagtggcag ggaggatgag cgcctgcgct gtgccgagct ggagagggag gttgcggagc     900
tgcagcaccg gaaccaggcg ctgactagcc tggcccagga ggcacaggcc ctgaaggatg     960
agatggatga actacggcag tcttcggagc gtgctgggca gctggaggcc acgctgacca    1020
gttgccggcg ccgcttgggc gagctgaggg agctgcggcg gcaggtgcgg cagctggagg    1080
```

```
aacgcaacgc cggccacgcc gagcgcacgc gacaactgga ggatgagcta cgccgagcgg    1140
gctccctgcg cgcccagctg gaggcgcagc ggcggcaggt gcaggaactg cagggccagc    1200
ggcaggagga ggccatgaag gccgagaaat ggctatttga atgccgcaac ctggaggaaa    1260
agtatgagtc ggtgacaaag gagaaggagc ggctgttggc ggagcgggac tccttgcggg    1320
aggccaatga ggagctgcgc tgcgcccagc tgcagccgcg ggggttgacc caggccgatc    1380
cctcactgga tcccacctcc acaccgtgga ataacttagc cgcagagatc ctgcctgcgg    1440
agctcaggga gacgctcctg cggcttcagc tggagaacaa gcggctgtgc aggcaggagg    1500
cggccgaccg ggagcggcag gaggagctgc agcgccacct ggaggatgcc aaccgcgcgc    1560
gccacgggtt ggagacgcag caccggctga ccagcagca gctatccgag ctgcgggccc    1620
aggtggagga cctgcagaaa gccctgcagg agcagggggg caagactgaa gatgccattt    1680
ccattttgct gaaaaggaag ctggaggaac atttgcagaa gcttcatgag gcagatctgg    1740
agttgcagag gaagcgggag tacattgagg agctggagcc acccactgac agcagcacag    1800
cccggcggat cgaggagctg cagcataact tgcagaagaa ggacgcggac ttgcgggcca    1860
tggaggagca ataccgccgc tacgtggaca aggcccgcat ggtcatgcag accatggaac    1920
ccaagcagcg gccagctgcg ggggcacctc cagaactcca ttccctgagg acacagctcc    1980
gagaacggga tgtccgcatc cgacacctgg agatggactt tgagaaaagc cgaagtcagc    2040
gggagcagga agaaaagctg ctcatcagtg cctggtataa tatgggcatg gccttgcagc    2100
agcgagctgg ggaggagcgg gcgcctgccc atgcccagtc attcctggca cagcagcggc    2160
tggcaaccaa ttctcgccgt ggaccccttgg gacgcctggc atctctgaac cttcgcccca    2220
ctgacaagca ctgacagacc tcacaatcaa gccagcctgg gctccaccca ccctggcttc    2280
ctccagctca catggcgccc agcactgggc ttcagccagg tgctcgagag ctttgaggcc    2340
atgatctctg ctcttccctc tcccagattg gtggggaggg agggcgggag gtagatatag    2400
gcctgttctt tttagcaatg tgattcttgt tgttgattct ctctctggag ttcatgtgct    2460
gcctcaggag actctgattt tatatttgag aaaaataaag gcgttcaatc tgcaaaaaaa    2520
aaaaaaaa                                                              2528
```

<210> SEQ ID NO 14
<211> LENGTH: 671
<212> TYPE: DNA
<213> ORGANISM: Homo sapiens
<220> FEATURE:
<221> NAME/KEY: misc_feature
<223> OTHER INFORMATION: Incyte ID No:1871275CB1

<400> SEQUENCE: 14

```
gagagatata tggaaggaag ggaagtaagc agtcacagac gctggcggcc accagaagtt      60
tgagcctctt tggtagcagg aggctggaag aaaggacaga agtagctctg gctgtgatgg     120
ggatcttact gggcctgcta ctcctggggc acctaacagt ggacacttat ggccgtccca     180
tcctggaagt gccagagagt gtaacaggac cttggaaagg ggatgtgaat cttccctgca     240
cctatgaccc cctgcaaggc tacacccaag tcttggtgaa gtggctggta caacgtggct     300
cagaccctgt caccatcttt ctacgtgact cttctggaga ccatatccag caggcaaagt     360
accagggccg cctgcatgtg agccacaagg ttccaggaga tgtatccctc caattgagca     420
ccctggagat ggatgaccgg agccactaca cgtgtgaagt cacctggcag actcctgatg     480
gcaaccaagt cgtgagagat aagattactg agctccgtgt ccagaaacac tcctcaaagc     540
```

| | |
|---|---|
| tactcaagac caagactgag gcacctacaa ccatgacata ccccttgaaa gcaacatcta | 600 |
| cagtgaagca gtcctgggac tggaccactg acatggatgg ctagcttgga gagaccagtg | 660 |
| ctggggcagg a | 671 |

<210> SEQ ID NO 15
<211> LENGTH: 1146
<212> TYPE: DNA
<213> ORGANISM: Homo sapiens
<220> FEATURE:
<221> NAME/KEY: misc_feature
<223> OTHER INFORMATION: Incyte ID No:2645806CB1

<400> SEQUENCE: 15

| | |
|---|---|
| tacttccggg agagaatggg agggtggaaa attttgtgcg tttggcgggt ttcgctctct | 60 |
| tcataagtat tgatcattcc gcagccctgc ggaccggaca cgtgaggagg tagtgacgcc | 120 |
| gacactgcca gaacacactg ctacaaggtc ccagatggcc acgtctctgg attttaaaac | 180 |
| ttatgtagat caggcatgta gagctgctga ggagtttgtc aatatttact atgagacaat | 240 |
| ggataaaaga agacgggcac taaccaggct gtatctggac aaggccacct taatatggaa | 300 |
| tggaaatgct gtttcagggc tggatgccct aaataatttt tttgacacat tgccttctag | 360 |
| tgagttccag gtcaatatgt tagattgcca accagttcat gagcaagcaa ctcagtccca | 420 |
| aactacagtt cttgttgtga ccagtggaac tgtgaagttt gatggaaaca aacaacattt | 480 |
| cttcaaccag aacttcctgc tgactgctca gtccactccc aacaatactg tgtggaagat | 540 |
| tgcaagtgat tgcttccgtt ttcaagattg gtctagtagt taaaggggca aaagtccatt | 600 |
| ctcatttggt ccattagttc cagcaattga aatttatgtg aattattttg attgtagaag | 660 |
| cactataata tgtgctgaaa ctaaatttct ttaaatattt ctattcctgt cagcacctt | 720 |
| tctagcagct gccagtttgg agcattgccc tctaagagct ttaaaactat tttttttacat | 780 |
| gccttatata cattccacta atgacattct tataataata ttaaacacat gatcttggta | 840 |
| ctaacatact cactgtgaac ccagcctatt gcaaaaataa aatcttttta taatattatc | 900 |
| tatgggatgt cagcacaata taacactctg ggaagaagtg gagtttttg gttattaggt | 960 |
| taattttcta gtaaaacacg ttgcctgttt tcagttaaca ctggtaatgc catttaata | 1020 |
| tatggctttt tcaaatcagt tcagtgaaaa tagtacagat ttaggtttac ataactactc | 1080 |
| tgacatactg gaattgcata tagagatgtt cagtggtcgt ttttcatttt aagtaatttt | 1140 |
| tgtttt | 1146 |

<210> SEQ ID NO 16
<211> LENGTH: 1175
<212> TYPE: DNA
<213> ORGANISM: Homo sapiens
<220> FEATURE:
<221> NAME/KEY: misc_feature
<223> OTHER INFORMATION: Incyte ID No:3437773CB1

<400> SEQUENCE: 16

| | |
|---|---|
| gttacctatt ggtttgtttc tgcctatgtc tgtttctctc cctctaactg tgatggttag | 60 |
| agagagagat tggattggaa tccatctttt ttccctgtat cttctctcc ctgtgggtat | 120 |
| ccctgatttt ggctccatct ggtcagactt cctcttcaaa ttcctggtga ttggcagtgc | 180 |
| aggaactggc aaatcatgtc tccttcatca gttcattgag aataagttca acaggactc | 240 |
| caacccacaca atcggcgtgg agtttggatc ccggtggtc aacgtgggtg ggaagactgt | 300 |
| gaagctacag atttgggaca cggctggcca ggagcggttt cggtcagtga cgcggagtta | 360 |

-continued

```
ttaccgaggg gcggctggag ccctgctggt gtacgacatc accagccggg agacatacaa    420
ctcactggct gcctggctga cggatgcccg caccctggcc agccccaaca tcgtggtcat    480
cctctgtggc aacaagaagg acctggaccc tgagcgggag gtcactttcc tggaggcctc    540
ccgctttgcc caggagaatg agctgatgtt cctggagacc agcgctctca caggcgagaa    600
cgtggaggag gcgttcctca agtgtgcccg cactatcctc aacaagattg actcaggcga    660
gctagacccg gagaggatgg gctctggcat tcagtacggg gatgcgtccc tccgccagct    720
tcggcagcct cggagtgccc aggccgtggc ccctcagccg tgtggctgct gagctctgtg    780
gagccagctc acctgttctc caggaccagc cctgctgggg cccaggccca ggctctgaga    840
ggccgtgtcc taacctgccc tggccccgga gaagctacgt tgccacctgt cccccttccc    900
tggcctggtg gggcctggct ttggggcaag actgagccac gggggaaggg ggaatcccgt    960
acctgctgct gcttcctctg tcttggctaa cgtctgtccc cctgaacccc taaccatatc   1020
ccaagagctc ccaaagcctg agaccagggt catttgtccc caactcccca tctggccctg   1080
ctgttgctag tacctgttat ttattacctg gaggcctgtc cagcacccac cctaccccca   1140
taaagcattg tttacacctg taaaaaaaaa aaaaa                              1175
```